(12) United States Patent
Cullen

(10) Patent No.: US 8,756,781 B2
(45) Date of Patent: Jun. 24, 2014

(54) RETOOLING DEVICE AND TOOL

(75) Inventor: Kevin Cullen, Mona Vale (AU)

(73) Assignee: Bresight PTY Limited, Ingleburn NSW (AU)

( * ) Notice: Subject to any disclaimer, the term of this patent is extended or adjusted under 35 U.S.C. 154(b) by 401 days.

(21) Appl. No.: 13/123,212

(22) PCT Filed: May 7, 2010

(86) PCT No.: PCT/AU2010/000537
§ 371 (c)(1),
(2), (4) Date: Apr. 7, 2011

(87) PCT Pub. No.: WO2010/127410
PCT Pub. Date: Nov. 11, 2010

(65) Prior Publication Data
US 2011/0203092 A1    Aug. 25, 2011

(30) Foreign Application Priority Data

May 8, 2009    (AU) .................................. 2009902036

(51) Int. Cl.
*B25B 27/00* (2006.01)
*B23P 17/00* (2006.01)

(52) U.S. Cl.
USPC .......................................... 29/401.1; 29/242

(58) Field of Classification Search
USPC ........ 29/401.01, 402.08, 403.1, 426.4, 426.5, 29/453, 242
See application file for complete search history.

(56) References Cited

U.S. PATENT DOCUMENTS

2004/0181169 A1    9/2004    Diamond et al.

FOREIGN PATENT DOCUMENTS

GB        2437669 A    10/2007

OTHER PUBLICATIONS

Breseight Pty Limited et al., "International Search Report and Written Opinion," Int'l Patent Application No. PCT/AU2010/000537, filed May 7, 2010 (Jul. 29, 2010), Australian Patent Office.

*Primary Examiner* — John C Hong
(74) *Attorney, Agent, or Firm* — Janet Sleath; Speckman Law Group PLLC

(57) ABSTRACT

A tool with replaceable parts is provided. In a preferred embodiment the hand tool comprises a set of hand operated pliers (10) that are adapted to have, removably attached to them, replaceable jaws (14 and 16) which are connected to handles (44 and 46) by means of connectors (18 and 16) which are in turn, adapted to be actuated by an actuating member of a retooling device (12). The retooling device (12) comes pre-loaded with the replacement jaws and connectors in one end of the retooling device. The retooling device first disengages the existing jaws (16 and 14) and connectors (18 and 16) whereupon they are securely stored one end of the retooling device (12), and whereafter, the remaining portions of the pliers (10) are inserted into another end of the retooling device (12) where the preloaded jaws and connectors are attached.

8 Claims, 28 Drawing Sheets

RETOOLING DEVICE AND TOOL

TECHNICAL FIELD

The present invention relates generally to tools and, more particularly, to a retooling device for removing and replacing used heads of tools including hand tools.

BACKGROUND ART

Hand tools have heads which are subject to wear over time. For instance, in the dental industry, pliers need to be repaired or replaced after as little as 12 weeks of extensive use.

A problem with used prior art hand tools, particularly with pliers in the medical industry, is that there is a shortage of skilled sharpeners. Blunt instruments often need to be sent overseas to a skilled sharpener for several weeks at a time. Another problem with prior art hand tools is that regularly disposing and replacing them is not cost effective.

While tools with replaceable heads are known in the art, there is a need for a device which can accurately and reliably remove and replace the heads of precision hand tools. Moreover, there is also a need for a device which can remove and replace a used head of a hand tool in a hygienic fashion for use in sterile and/or aseptic environments, such as in the dental or medical industries, without a user having to touch the new head of the hand tool.

DISCLOSURE OF INVENTION

Accordingly, a first object of the present invention is to provide a hand tool with a replaceable head. A second object of the present invention is to provide a device for removing and replacing used heads on hand tools.

According to a first aspect of the invention there is provided a tool adapted to engage a retooling device for replacing one or more removeably attached parts of the tool.

Preferably, the tool is a hand tool that has one or more parts which are removeably attached via connecting means.

Still more preferably, the one or more parts of the tool comprises a removeably attachable head which is attached to the tool via a connector that is actuated by an actuating member of the retooling device.

Even more preferably, the tool is adapted such that the connector of the tool is actuated by the actuating member of the retooling device when force is applied to the tool which causes the connector to become biased against the actuating member of the retooling device.

Preferably, the tool is adapted to engage the retooling device such that both removal and attachment of the one or more parts of the tool to be replaced can be effected with the one retooling device.

More preferably, the tool is a hand tool.

Preferably, the hand tool is a set of pliers and the one or more replacement parts comprises the head of the pliers.

According to a second aspect of the invention, there is provided a retooling device for removing and replacing one or more removably attached parts of a tool that is adapted to engage the retooling device, the retooling device comprising at least an actuating member for engaging a connector of the tool that when actuated detaches the one or more removeably attached parts of the tool that are to be replaced.

Preferably, the retooling device comprises means to capture the used head of the hand tool.

Still more preferably, the retooling device has a body which is adapted to store the one or more replacement parts of the tool inside of the retooling device.

More preferably, the retooling device is adapted such that the loaded one or more replacement parts can be applied to the tool without touching the one or more replacement parts.

Still more preferably, the retooling device is adapted to receive a suitably adapted tool with one or more removeably attached parts for removal at one end where the parts are detached, and stored in the body of the retooling device, and at a second end, receive the remaining portion of the tool and attach the replacement parts.

In a third aspect of the invention, there is provided a retooling system comprised of a retooling device and a tool adapted to engage the retooling device such that the tool can have one or more removeably attached parts first detached then replaced with replacement parts by insertion into one or more ends of the retooling device.

Preferably, the system provides the means for replacing the one or more replacement parts without the user touching them.

According to a fourth aspect of the invention, there is provided a method of retooling a tool in need or replacement parts, the method comprising:

inserting the tool into one end of a retooling device and actuating the device to detach the one or more parts to be replaced;

removing the tool and inserting it into a second end of a retooling device and actuating the tool to attach the one or more replacement parts, removing the tool from the retooling device with the replacement parts attached.

Preferably, the tool is a tool with a set of pivoting handles and actuating the retooling device involves applying force to the handles such that one or more connectors of the tool becomes biased against one or more actuating members of the retooling device.

More preferably the tool is a set of pliers.

BEST MODE FOR CARRYING OUT THE INVENTION

Figure 1:
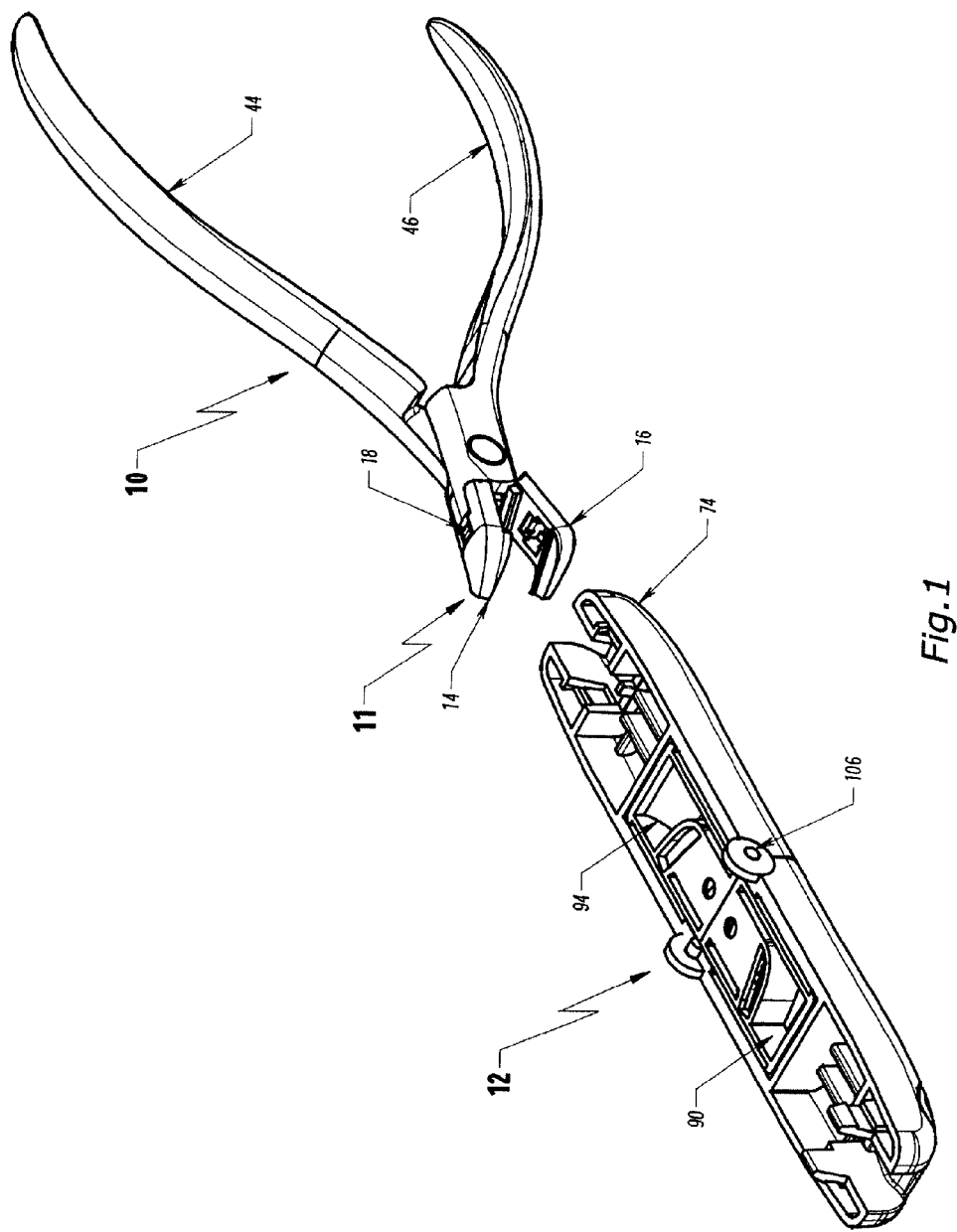
FIG. 1 is a perspective view of a hand tool and retooling device according to an embodiment of the present invention.
Figure 2:
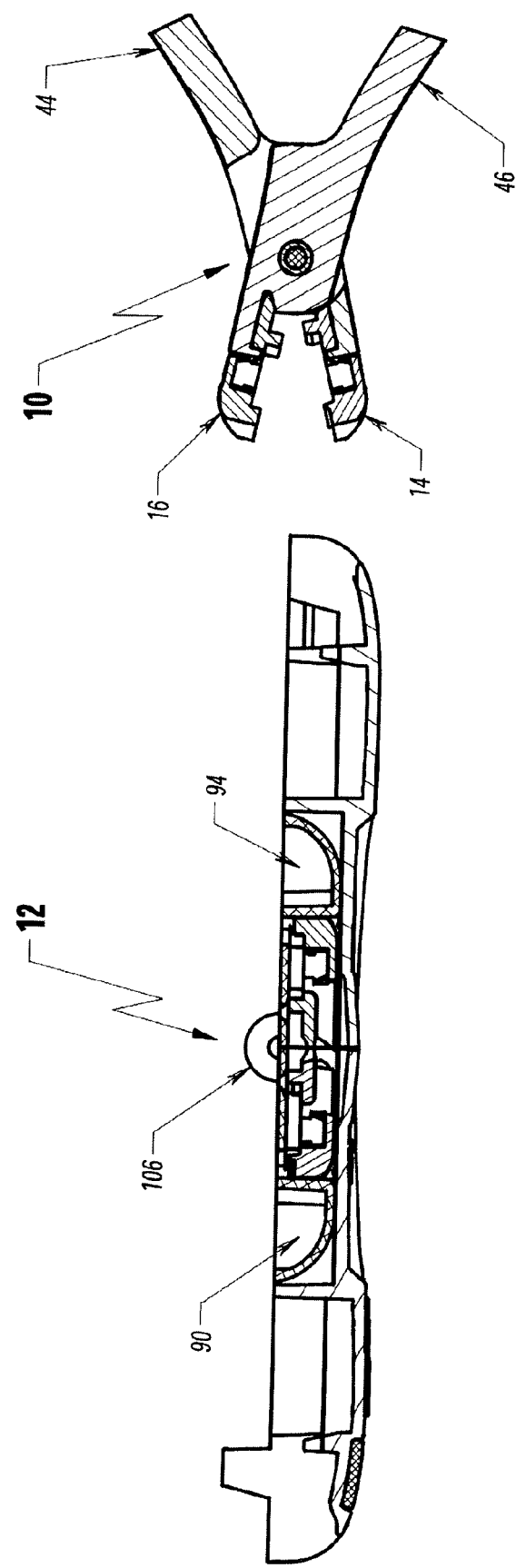
FIG. 2 is a cross-sectional view of the hand tool and retooling device of FIG. 1, wherein the hand tool is open and the retooling device is open.
Figure 3:
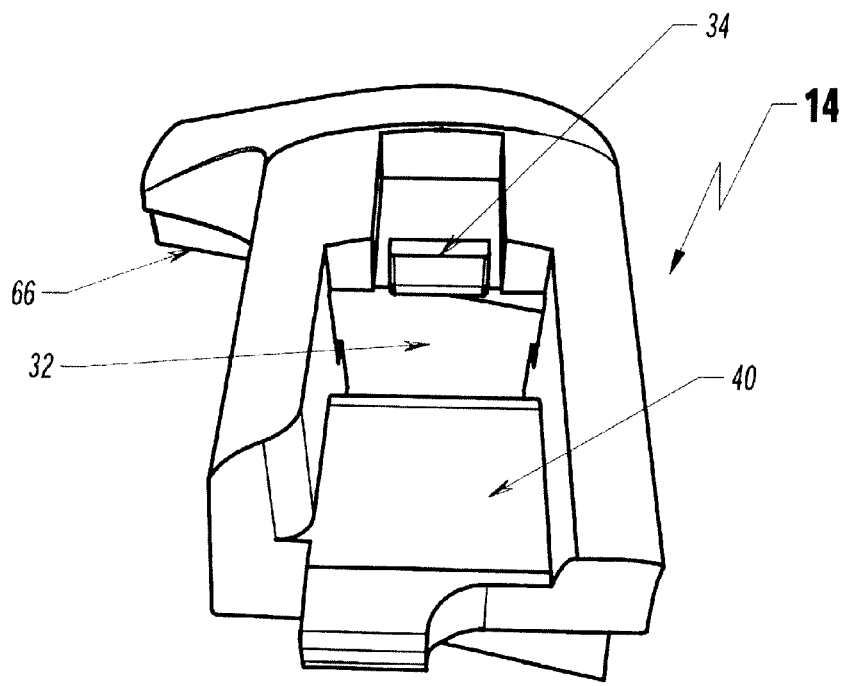
FIG. 3 is a perspective view of the top jaw of the head of the hand tool of FIG. 1.
Figures 4, 5:
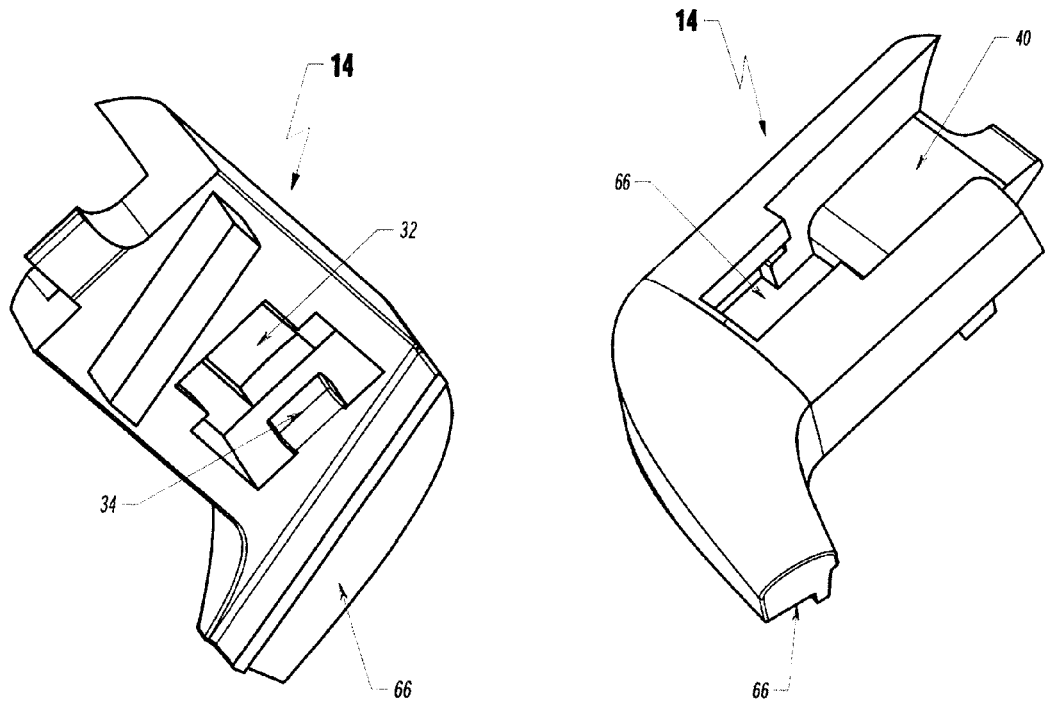
FIG. 4 is another perspective view of the top jaw of the head of the hand tool of FIG. 1.
FIG. 5 is yet another perspective view of the top jaw of the head of the hand tool of FIG. 1.
Figure 7:
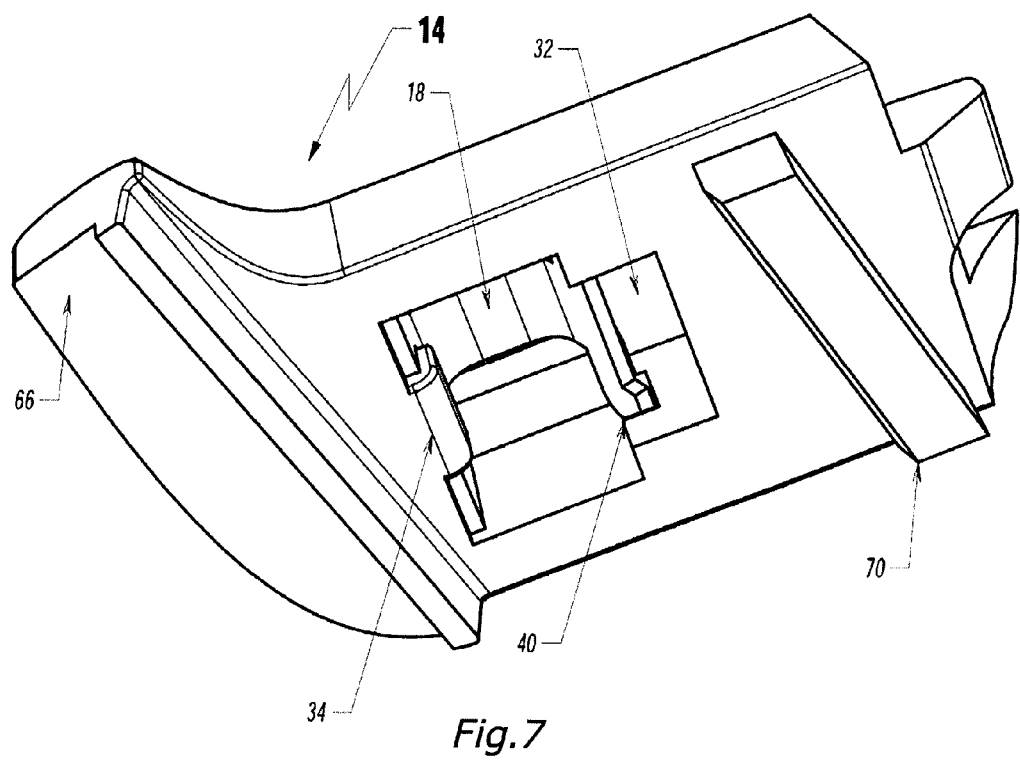
FIG. 7 is a perspective view of the spring connector and top jaw of the hand tool of FIG. 1.
Figure 8:
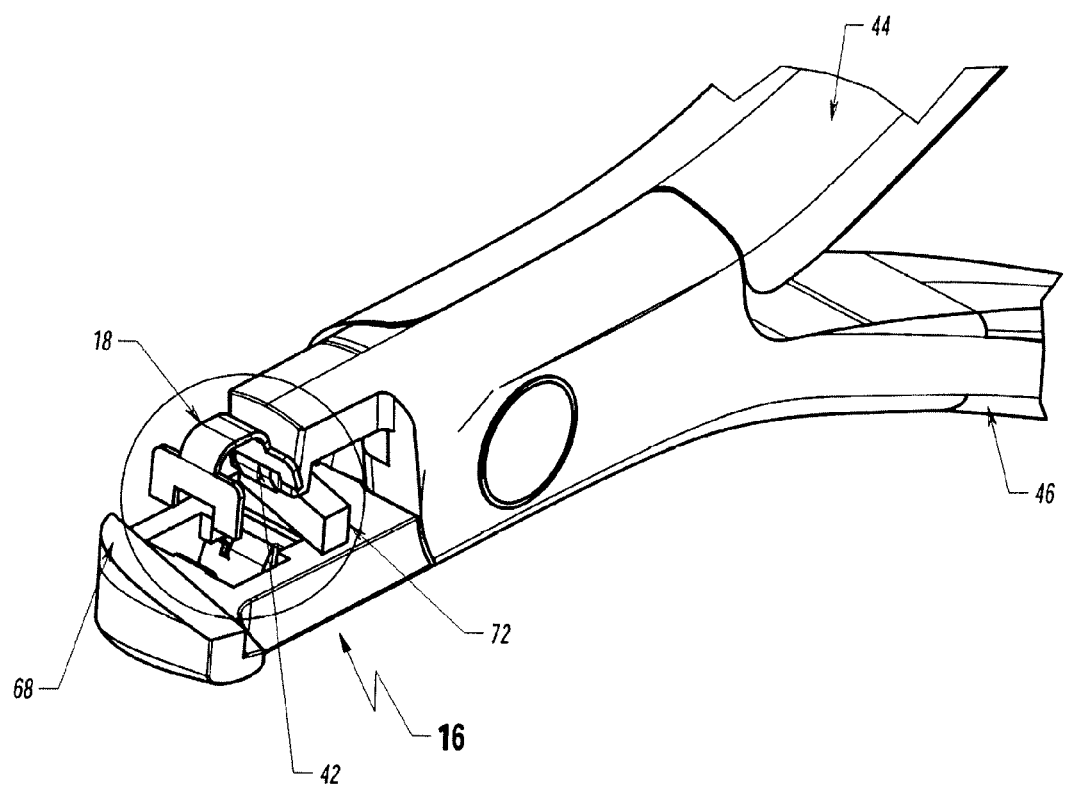
FIG. 8 is a perspective view of the spring connector and hand tool of FIG. 1, with the top jaw of the hand tool removed.
Figure 16:
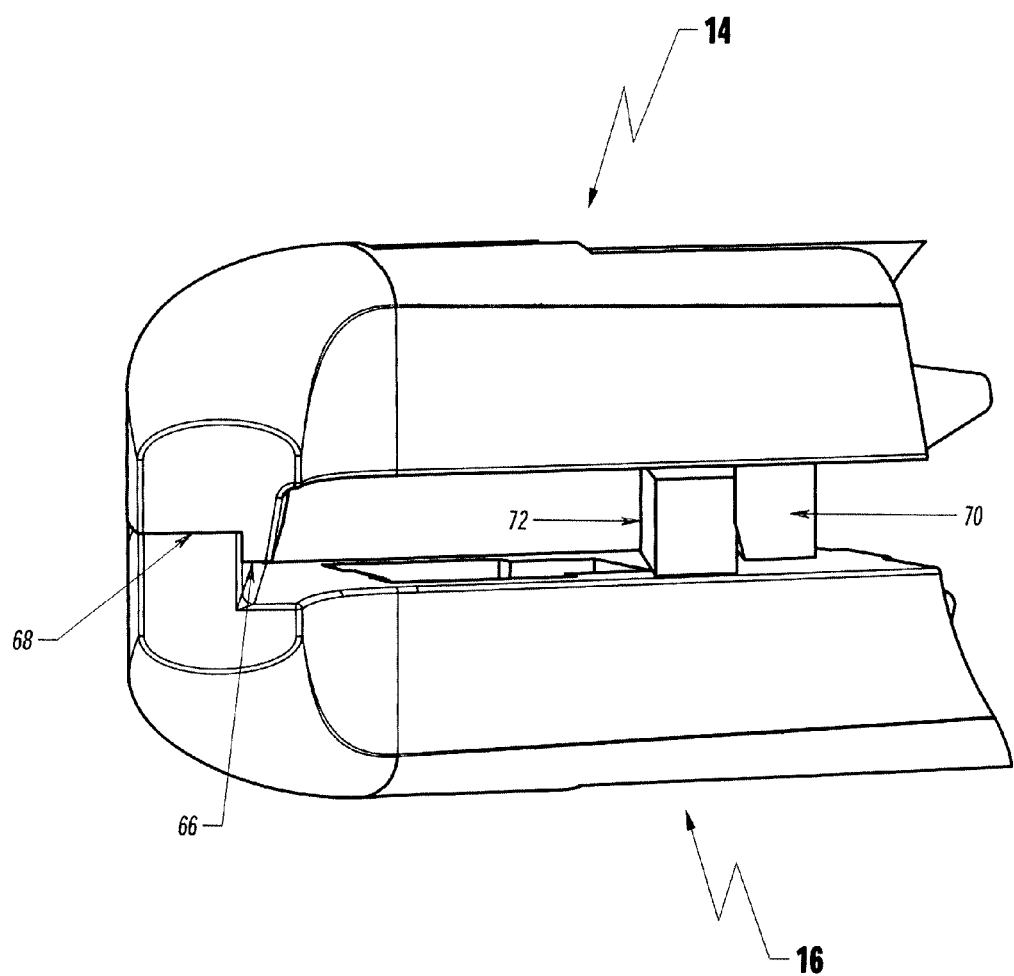
FIG. 16 is a perspective view of the jaws of the hand tool of FIG. 1.
Figure 17:
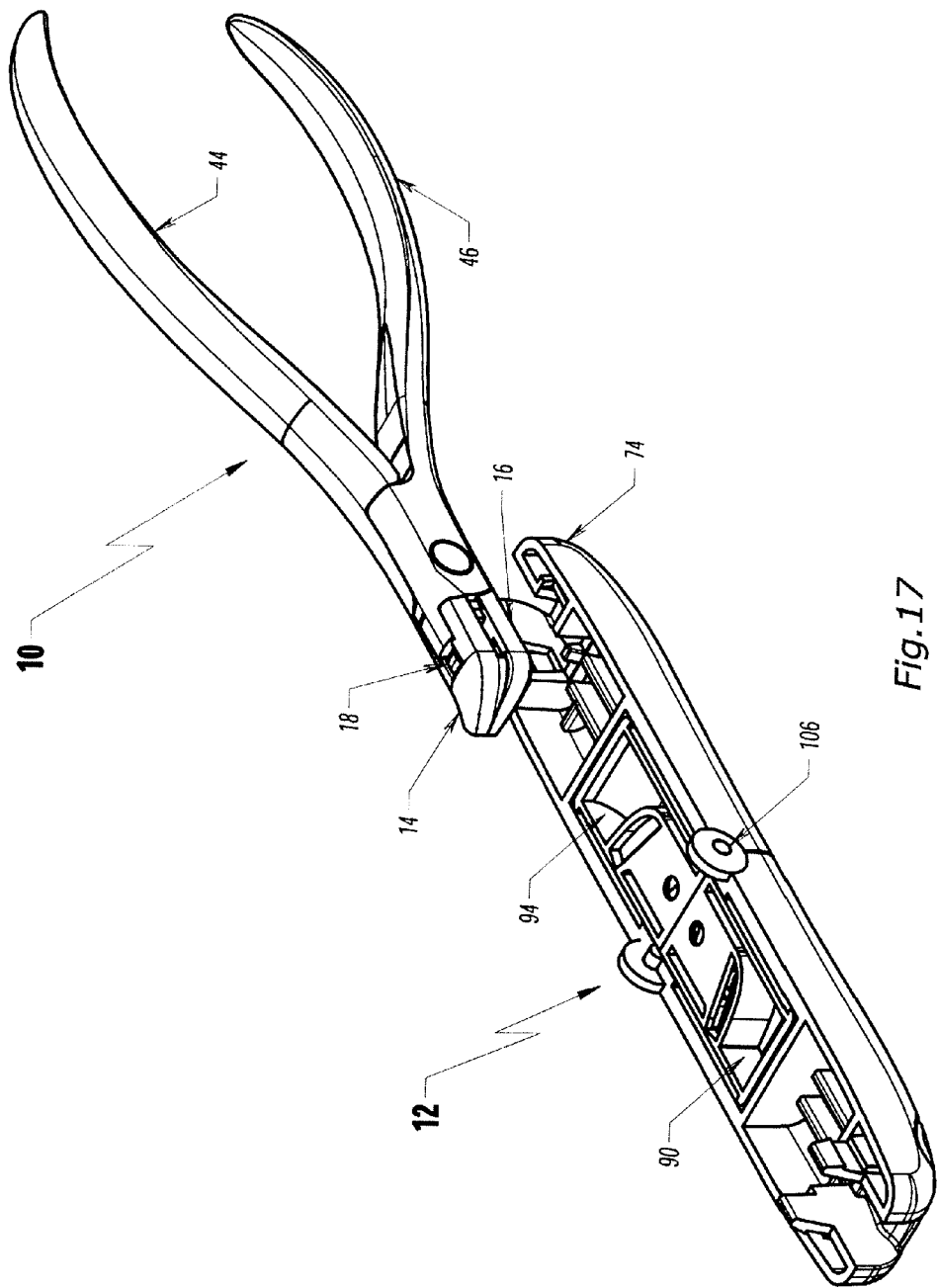
FIG. 17 is a perspective view of the hand tool and retooling device of FIG. 1, wherein the hand tool is closed.

FIGS. 1 and 2 show a hand tool 10 and a retooling device 12. In this embodiment of the invention, the hand tool 10 takes the form of a pair of pliers. A replaceable head 11 of the tool 10 comprises an upper jaw 14 and a lower jaw 16. The upper jaw 14 is shown in FIGS. 3, 4 and 5. The lower jaw 16, shown in FIG. 8, is generally a mirror image of the upper jaw 14 however there are some differences between them including overlapping cutting surfaces 66 and 68 as depicted in FIG. 16 and overlapping guides 70 and 72 as shown in FIG. 16 and FIG. 7.

Figure 6:
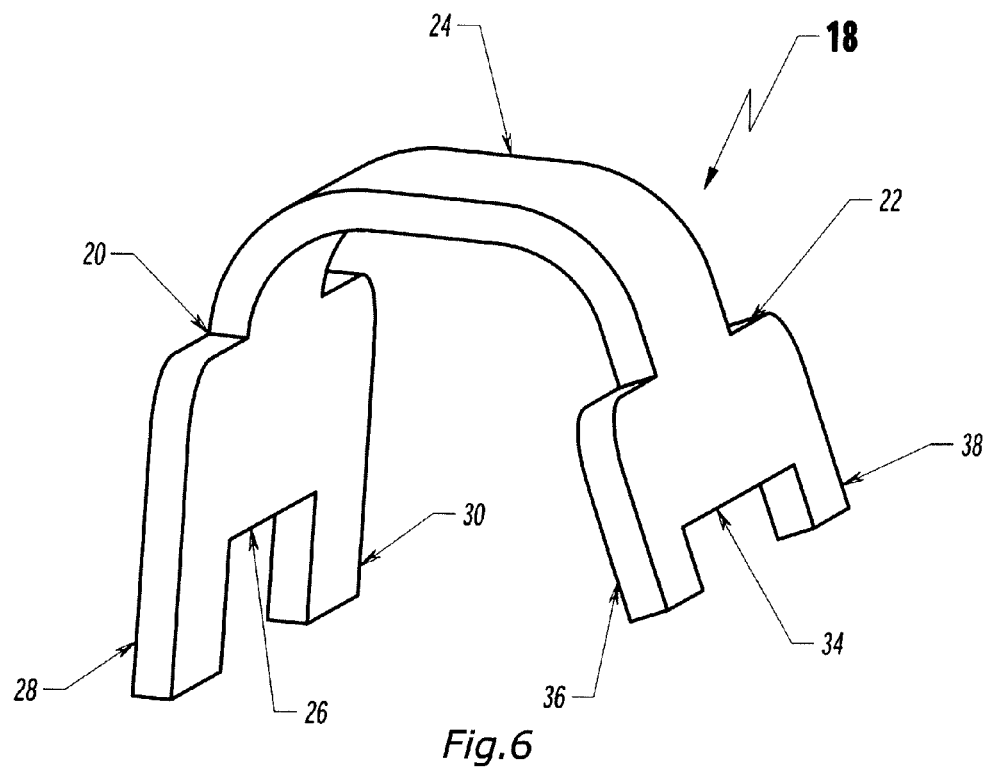
FIG. 6 is a perspective view of a spring connector used in the hand tool of FIG. 1.

A spring connector 18, shown in FIG. 6, has a first end 20 and a second end 22 which are connected by spring section 24. The first end 20 has a notch 26 flanked by two prongs 28 and 30. The first end 20 is lowered into an aperture 32 (see FIG. 3) in the upper jaw 14 and then pushed into position so that the notch 26 rests on a shelf 34 and the first end 20 is trapped within the upper jaw 14 as shown in FIG. 7.

The second end 22 of the spring connector 18 also has a notch 34 flanked by prongs 36 and 38. The prongs 36 and 38 rest on a shelf 40 within the upper jaw 14 as depicted in FIG. 7. In use, the notch 34 of the spring connector 18 traps a ledge 42 on a handle 44 (see FIG. 8).

Figure 9:
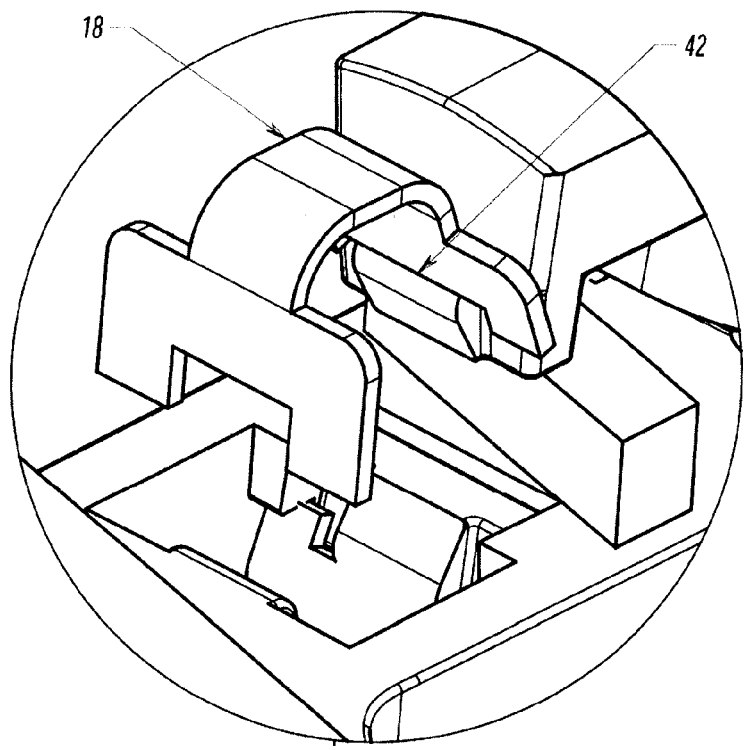
FIG. 9 is a close up view of a section of FIG. 8.
Figure 21:
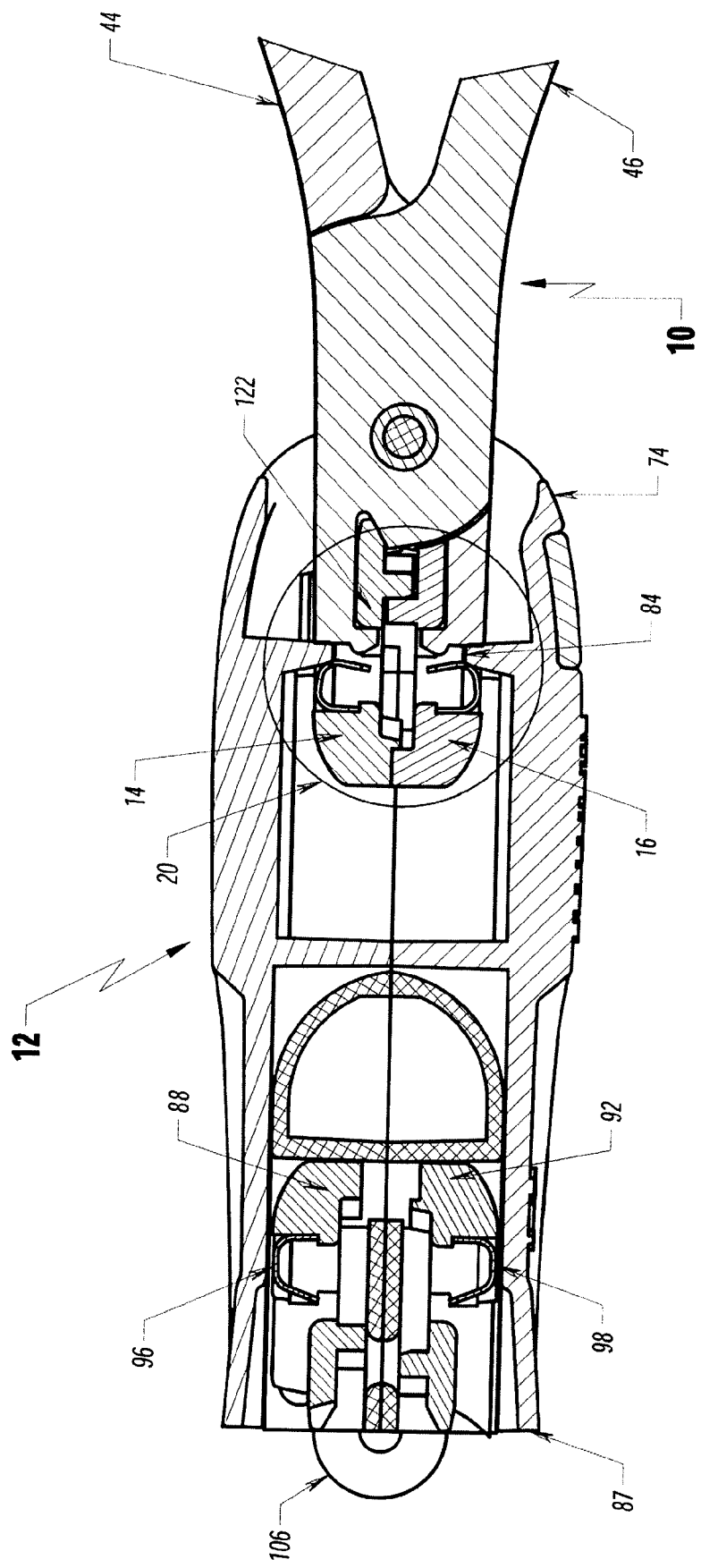
FIG. 21 is a cross-sectional view of FIG. 19.

Referring to FIG. 21, the second end 22 of the spring connector 18 biases the ledge 42 (see FIG. 9) away from the first end 20 of the spring connector 18 seated in the upper jaw 14. This results in the biasing of a jaw portion 122 towards a portion 118 of the handle 44 at surface 120 (see FIG. 22). It is these biased members which connect and keep connected the upper jaw 14 to the handle 44.

Figure 34:
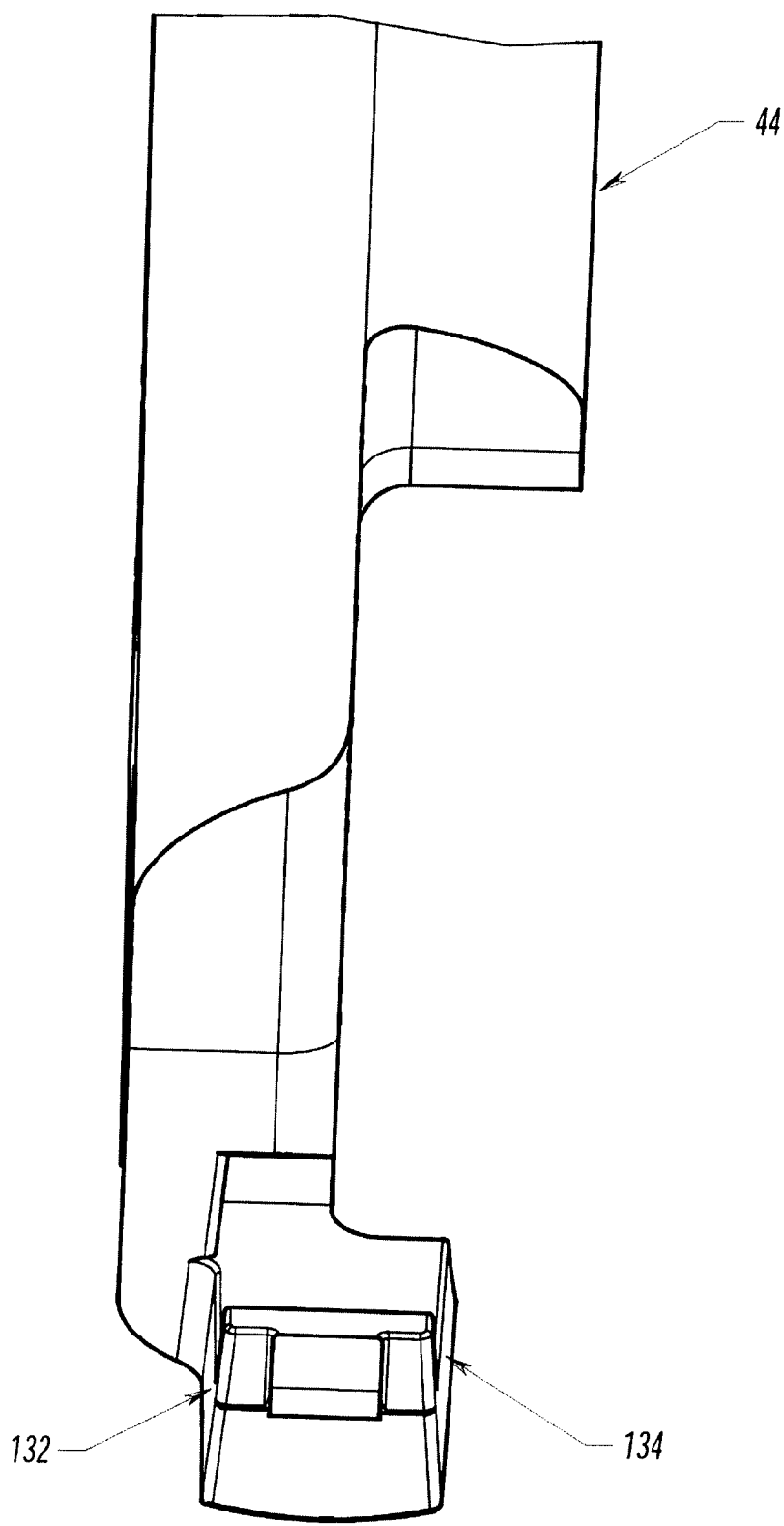
FIG. 34 is a front perspective view of the handle of the tool of FIG. 1.
Figure 35:
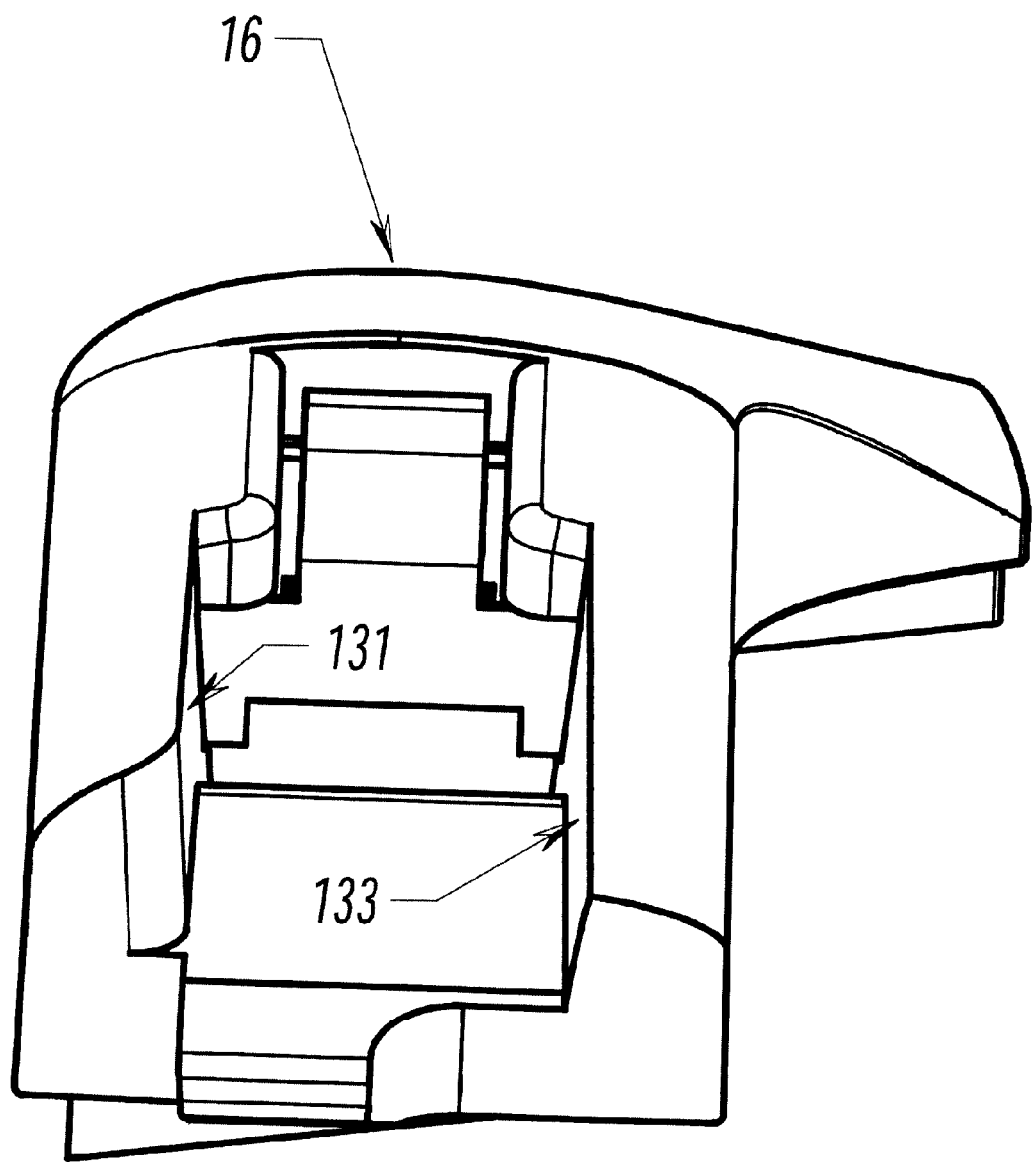
FIG. 35 is a rear perspective view of jaw of the tool of FIG. 1.

This biasing action also completes the biasing in FIG. 35 of surfaces 131 and 133 of the jaw 16 against surfaces 132 and 144 (see FIG. 34) of the handle 44. Surfaces 131 and 133 of the jaws are inclined at a small included angle. Surfaces 132 and 134 of the jaw are inclined at the same angle. The angle is sized so as to ensure adequate stability of the connected jaw and handle under the forces applied during operation despite inaccuracies of manufacture.

A feature of the invention is that the spring connector 18 cannot be dislodged by forces however arising between any surfaces of the jaw 14, the handle 44 and the spring connector 18. Thus, except for deformation of the spring connector 18 by some external device such as the retooling device 12 in FIG. 1, the components of the jaw 14 can come apart only if the material of the spring connector 18 is sheared through at zones such as the prongs 28, 30, 36, and 38 or shearing away of material of the shelf 34 of jaw 14 in FIG. 3 or shearing of the material 118 of the handle 44 in FIG. 22 or the shearing of material of the portion 122 of the jaw 14 in FIG. 22.

Figure 10:
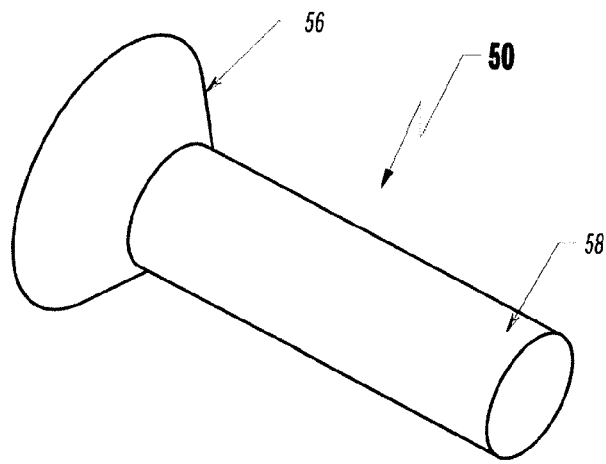
FIG. 10 is a perspective view of a pivot pin of the hand tool of FIG. 1.
Figure 11:
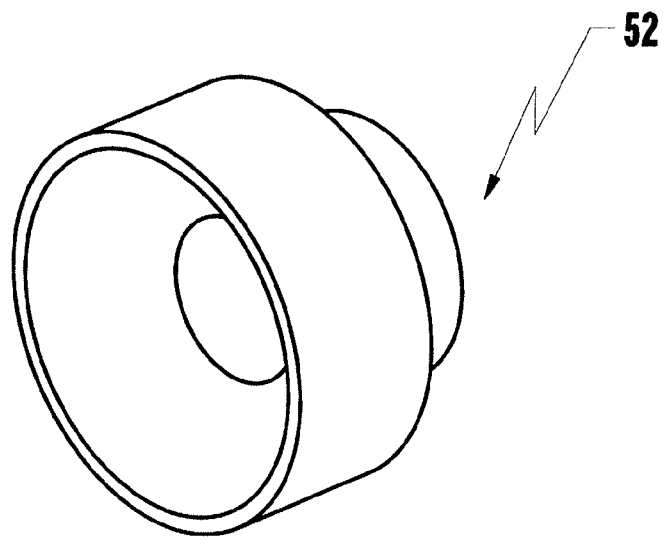
FIG. 11 is a perspective view of a bearing for the pivot pin of FIG. 10.
Figure 12:
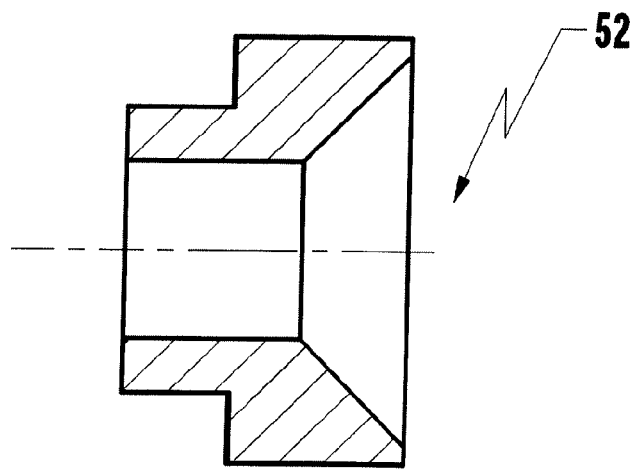
FIG. 12 is a side cross section view of the bearing of FIG. 11.

In order to connect the handle 44 to a handle 46, a pivot pin 50 (shown in FIG. 10) is inserted through a first bearing 52 (shown in FIGS. 11 and 12), which is placed within a pivot socket 54 (see FIG. 15) of the handle 44. The pivot pin 50 is solid and has a head 56 and a cylindrical shaft 58.

Figure 13:
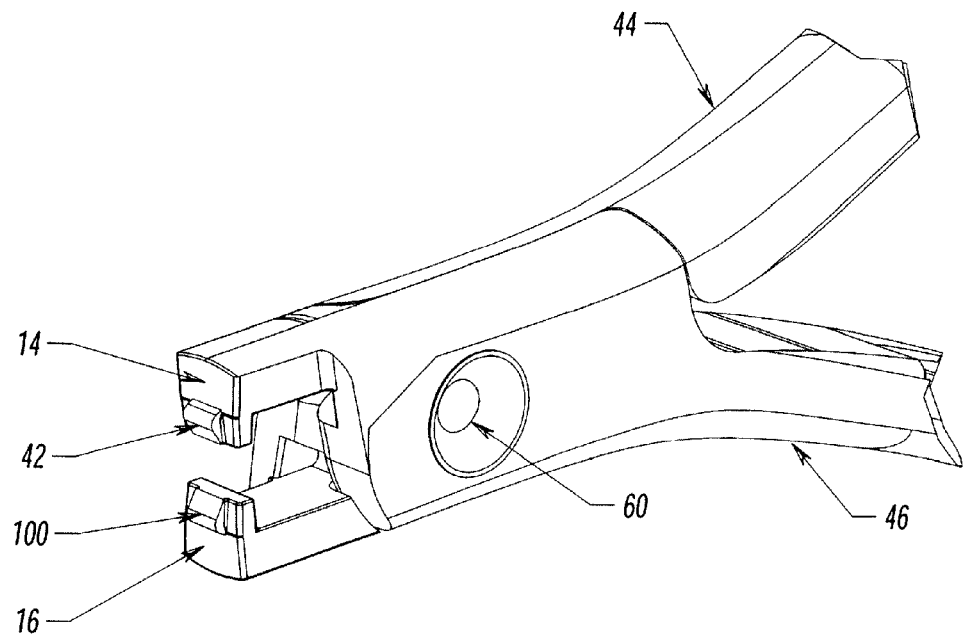
FIG. 13 is a perspective view of the hand tool of FIG. 1 with no jaws and no pivot pin.
Figure 14:
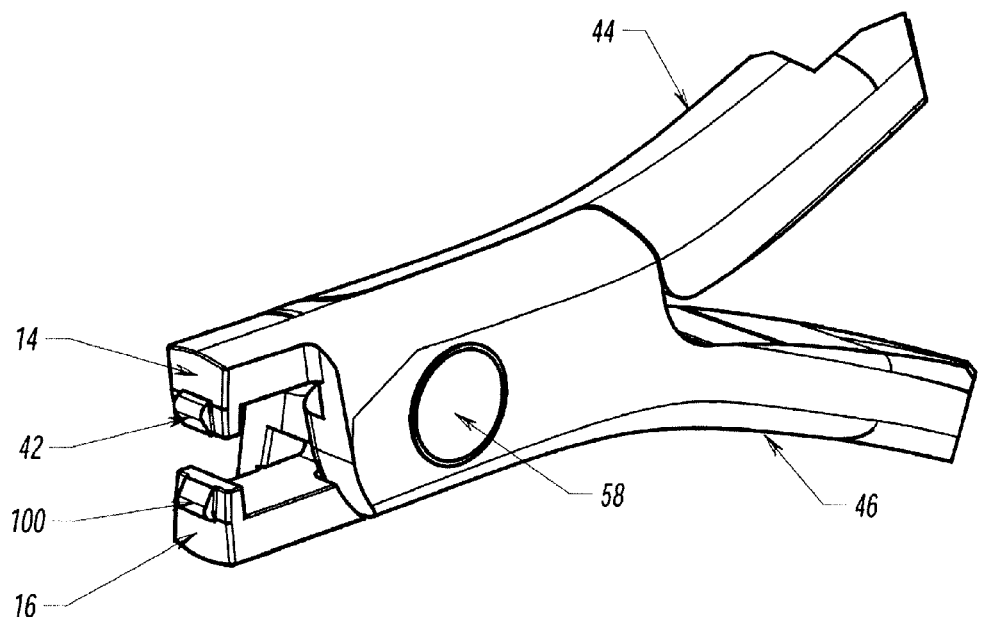
FIG. 14 is a perspective view of the hand tool of FIG. 12 with a pivot pin.
Figure 15:
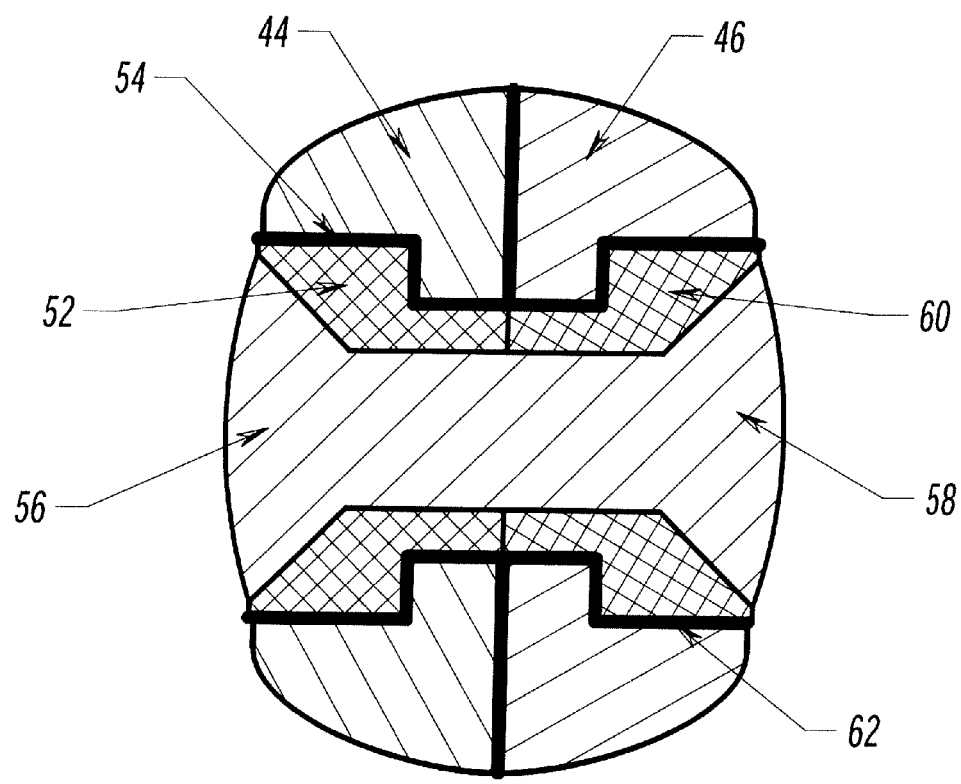
FIG. 15 is a cross section view of the pivot pin in place within the hand tool of FIG. 1.

The pivot pin 50 is then inserted through a second bearing 60 (see FIG. 13) which is placed within a pivot socket 62 (see FIG. 15) in the handle 46 which is aligned parallel with the handle 44. Once the cylindrical shaft 58 has been inserted through the second bearing 60, the head 56 and shaft 58 are pressed together or squashed so that the deformed shaft 58 fills the second bearing 60, as shown in FIGS. 14 and 15.

The advantage of attaching the handle 44 to the handle 46 in this manner is that it provides an extremely stable pivot mechanism for the hand tool 10. In another embodiment of the invention, the pivot pin 50 may comprise a cylindrical shaft 58 without the head 56, whereupon both ends of the cylindrical shaft 58 must be deformed so that they fill the bearings 52 and 60. Other methods of attaching the two handles 44 and 46 are within the scope and ambit of the invention, such as affixing a nut (not shown) to the cylindrical shaft 58 of the pivot pin 50, which may take the form of a screw. However, it has been found that using this method of attaching the two handles 44 and 46 eventually results in the loosening of the nut. If this occurs, the handle 44 and 46 may not be aligned parallel to each other and may therefore wobble when opening and closing the hand tool 10.

If the handles 44 and 46 are not aligned parallel to each other, then the cutting surface 66 of the upper jaw 14 will not correctly overlap with the cutting surface 68 of the lower jaw 16 (see FIG. 16) in order to effectively shear an object, such as a wire (not shown) in dental braces.

As shown in FIG. 16, the upper jaw 14 features an alignment member 70 and the lower jaw 16 features an alignment member 72. The alignment members 70 and 72 have chamfered edges adapted to slidably engage as the head 11 is closed. The alignment members 70 and 72 are a fixed distance from the cutting surfaces 68 and 70. When the alignment members 70 and 72 are aligned with one another, the cutting surface 66 of the upper jaw 14 will correctly overlap with the cutting surface 68 of the lower jaw 16.

When it is necessary to replace a used head 11 of the tool 10, the user removes a new aseptically clean or sterile retooling device 12 from its packaging (not shown) which comes loaded with a new head comprising of a new upper jaw 88 and new lower jaw 92 and associated spring connectors 96 and 98 carried in drawers 90 and 94 (see FIGS. 1 and 2). The pre-loaded new head is sterile or aseptically cleaned prior to packaging under aseptically clean or sterile conditions.

Figure 18:
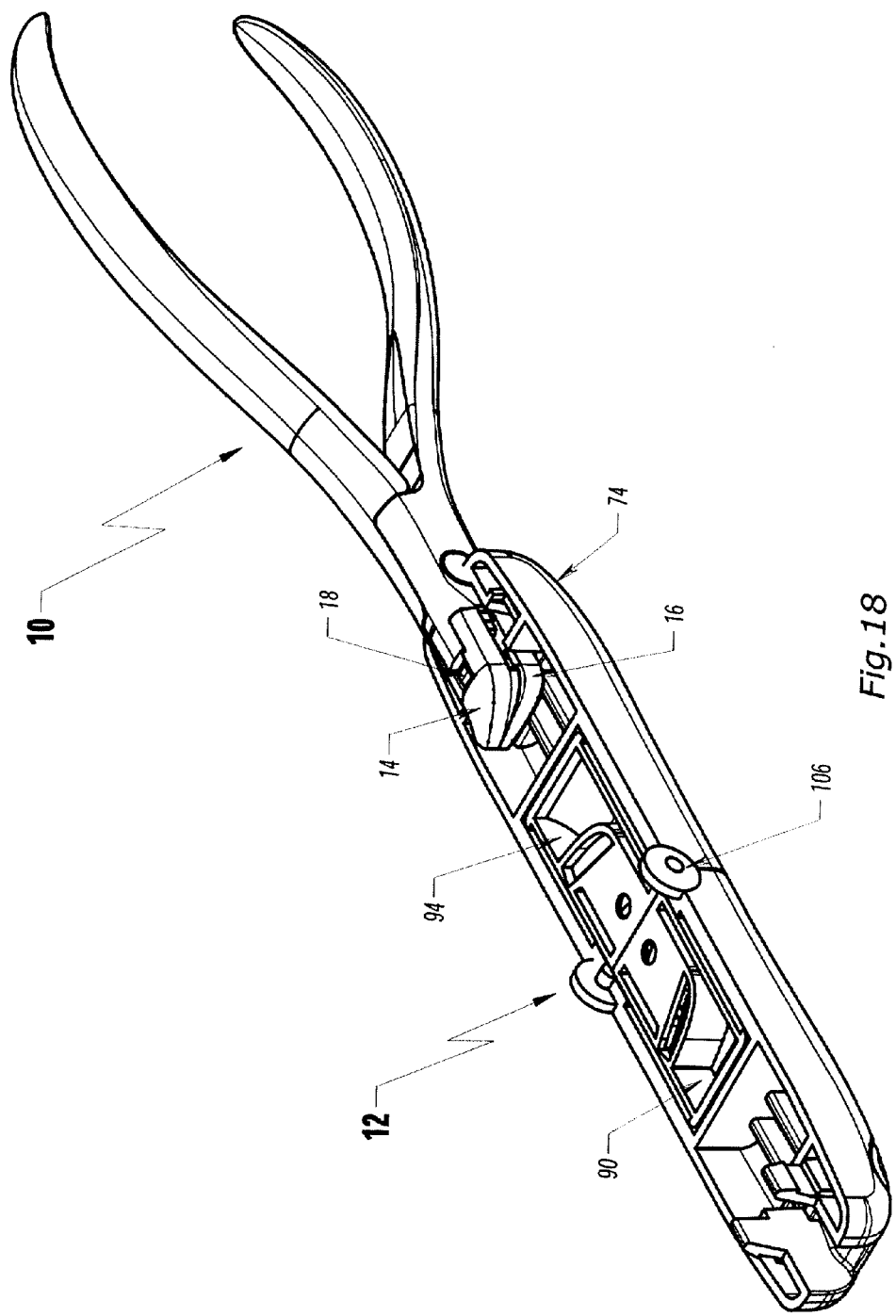
FIG. 18 is a perspective view of the hand tool and retooling device of FIG. 1, wherein the hand tool is closed and in-position within the removal side of the open retooling device.
Figure 19:
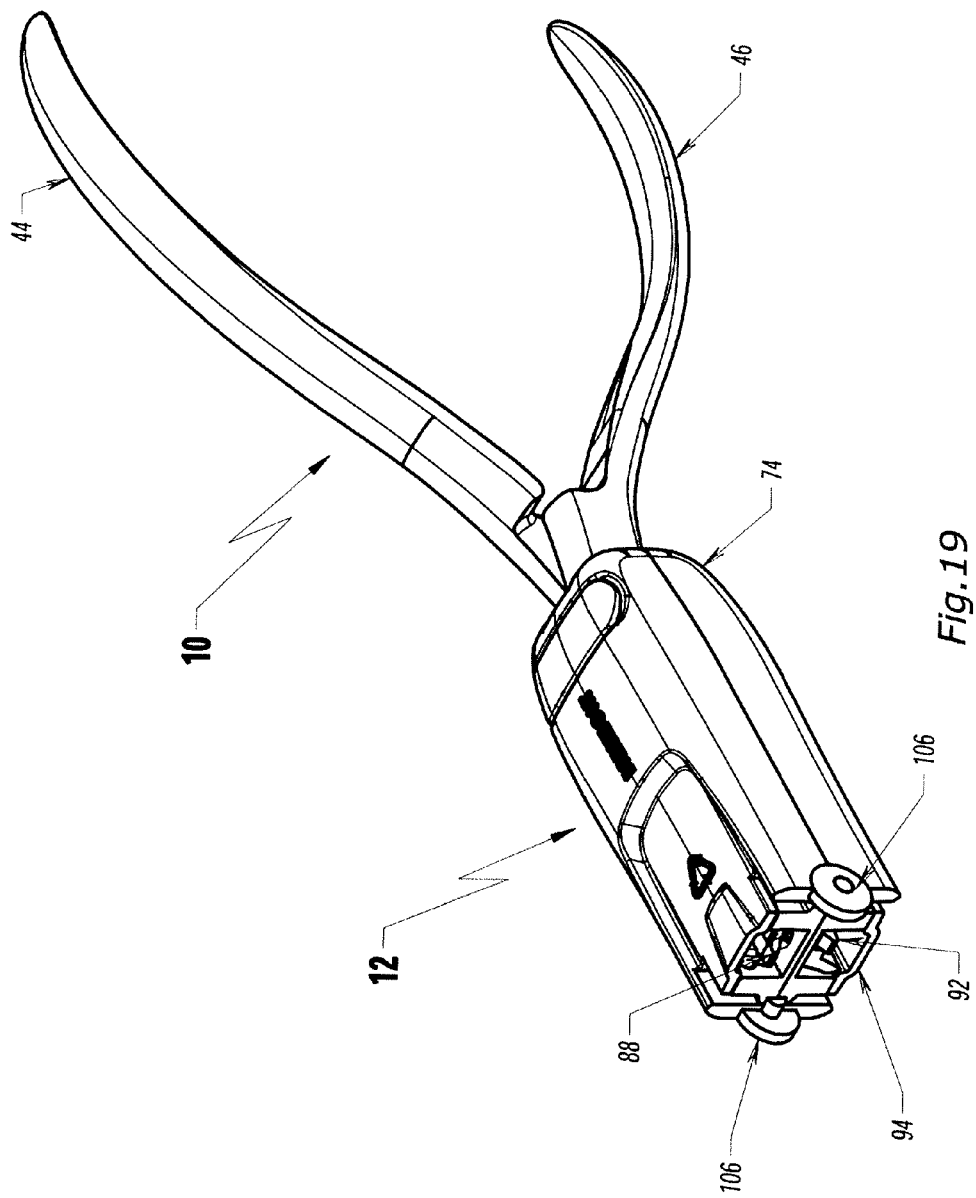
FIG. 19 is a perspective view of the hand tool and retooling device of FIG. 1, wherein the hand tool is open and in-position within the removal side of the closed retooling device.
Figure 20:
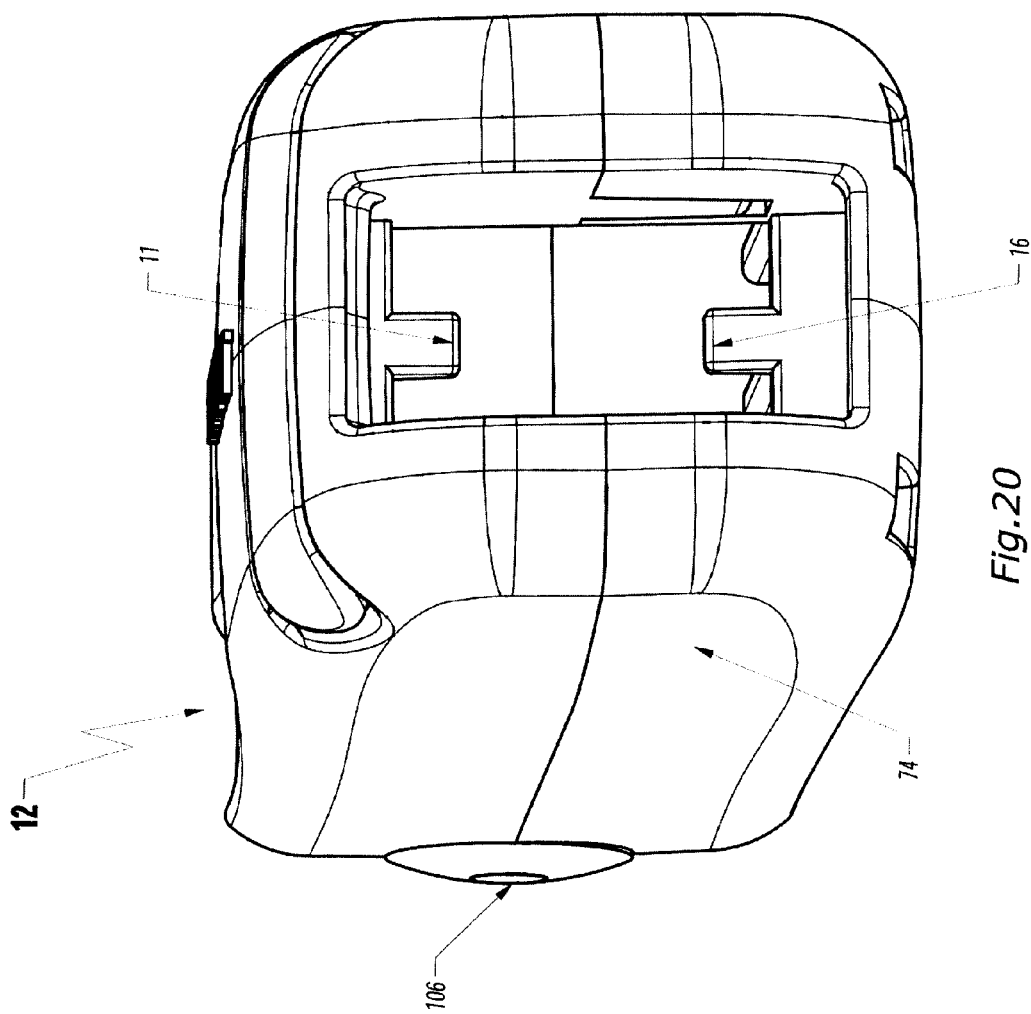
FIG. 20 is a perspective view of the closed retooling device of FIG. 1.
Figure 22:
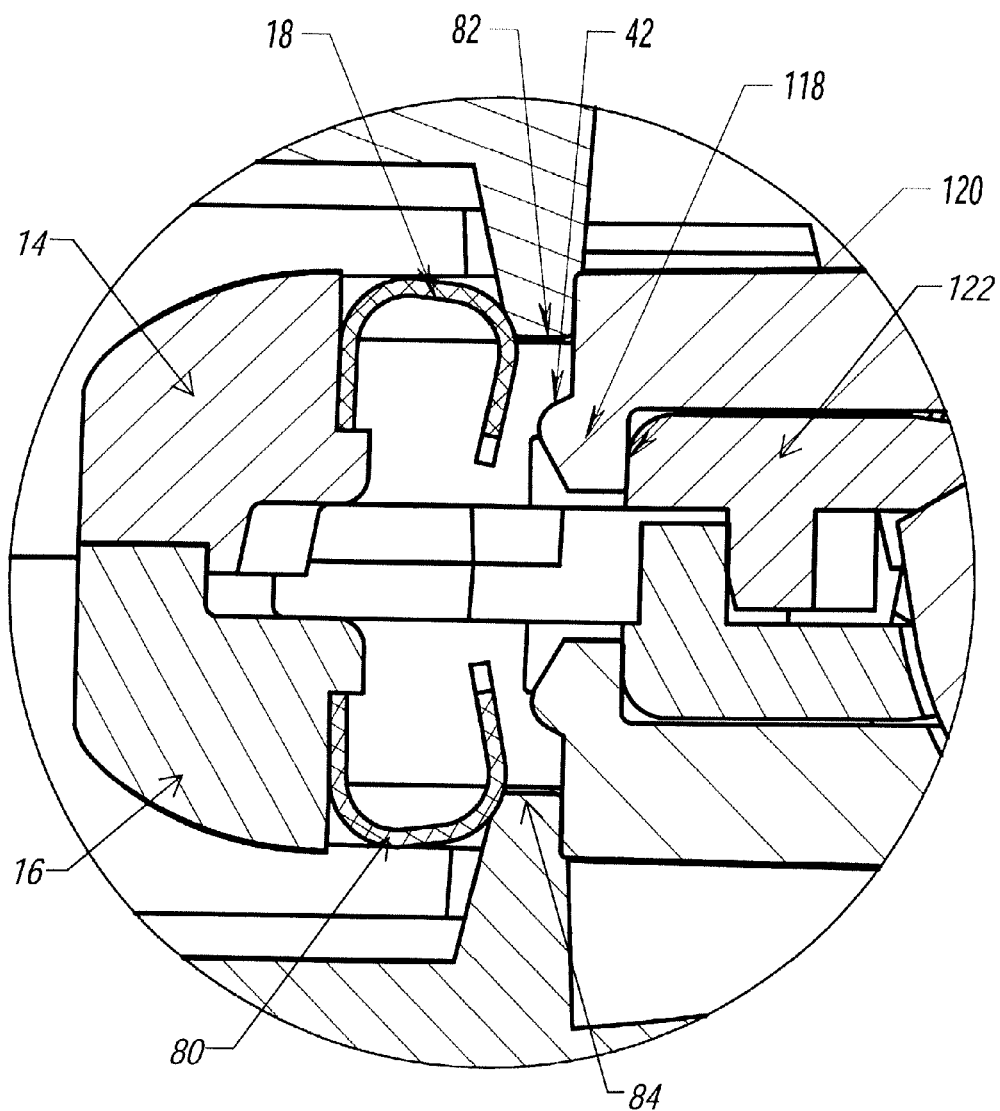
FIG. 22 is a close up view of a section of FIG. 21.

In order to remove the head 11 of tool 10, a user (not shown) lowers the hand tool 10 into position on a removal end 74 of the already open retooling device 12 as shown in FIG. 18, and closes the hand tool 10 as shown in FIG. 19. A perspective view of the closed retooling device 12 is shown in FIG. 20. A side-section view of the closed retooling device 12 is shown in FIG. 21. As shown in FIGS. 21 and 22, this causes the spring connectors 18 and 80 to be depressed by the first actuating members or flanges 82 and 84.

Figure 23:
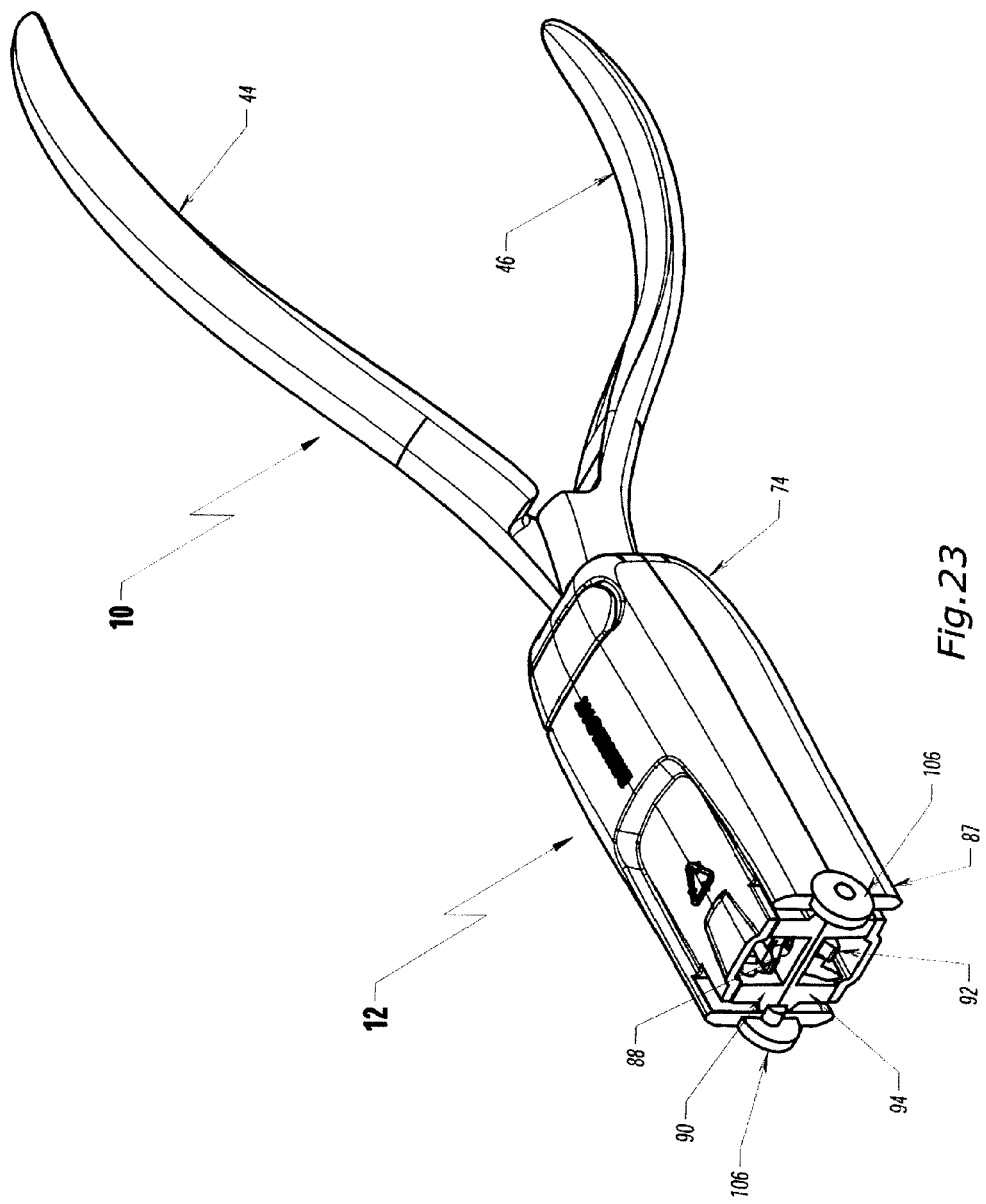
FIG. 23 is a perspective view of the hand tool and retooling device of FIG. 1, wherein the handles of the hand tool are being opened in order to remove the head from the hand tool.
Figure 24:
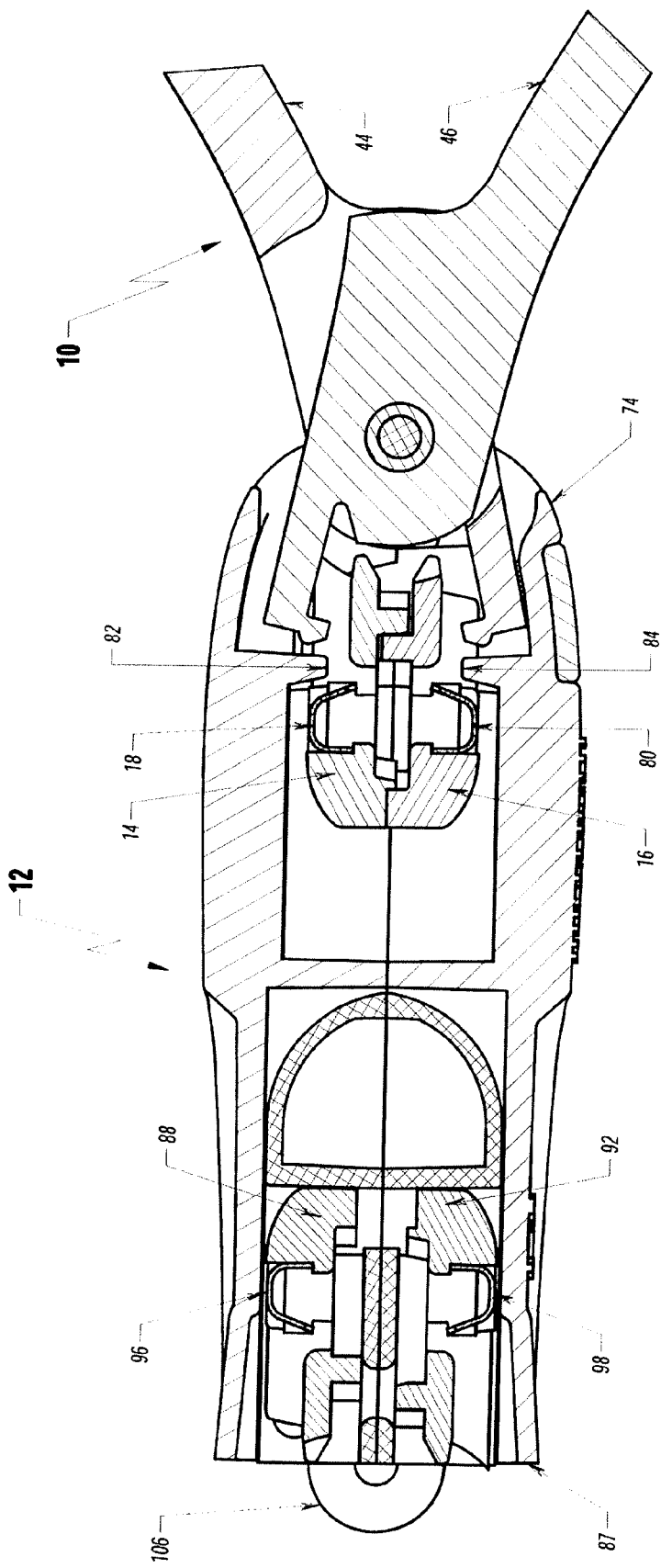
FIG. 24 is a cross-sectional view of FIG. 23.

Referring to FIGS. 23 and 24, a user may remove the used head 11 of the hand tool 10 by opening the handles 44 and 46, which releases the jaws 14 and 16 from the handles 44 and 46. In this way, the retooling device 12 captures the used head 11. The user may then remove the hand tool 10 from the retooling device 12 by closing and retracting the handles 44 and 46 from the retooling device 12.

Figure 25:
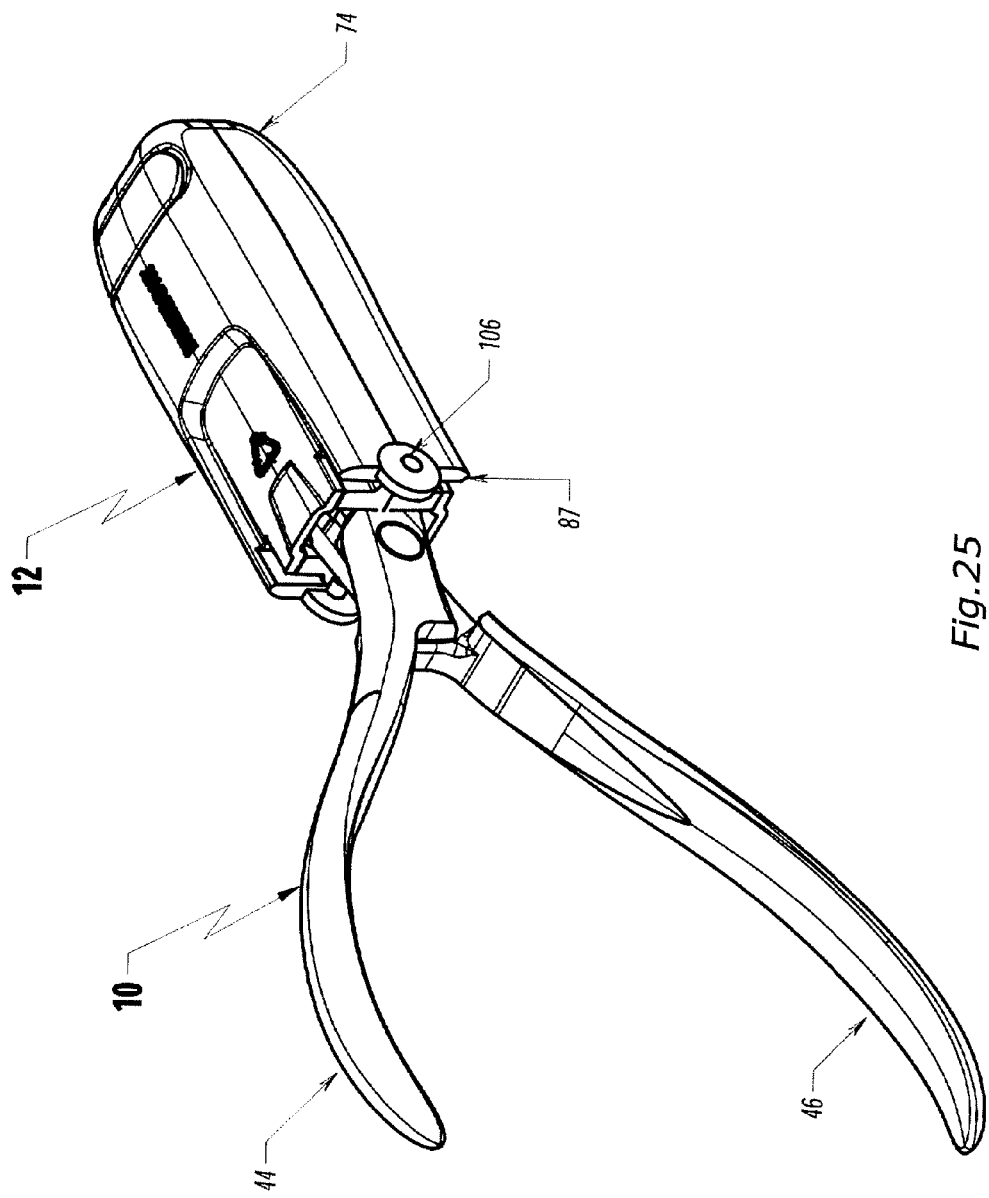
FIG. 25 is a perspective view of the hand tool and retooling device of FIG. 1, wherein the hand tool is being inserted into the attachment side of the closed retooling device.
Figure 26:
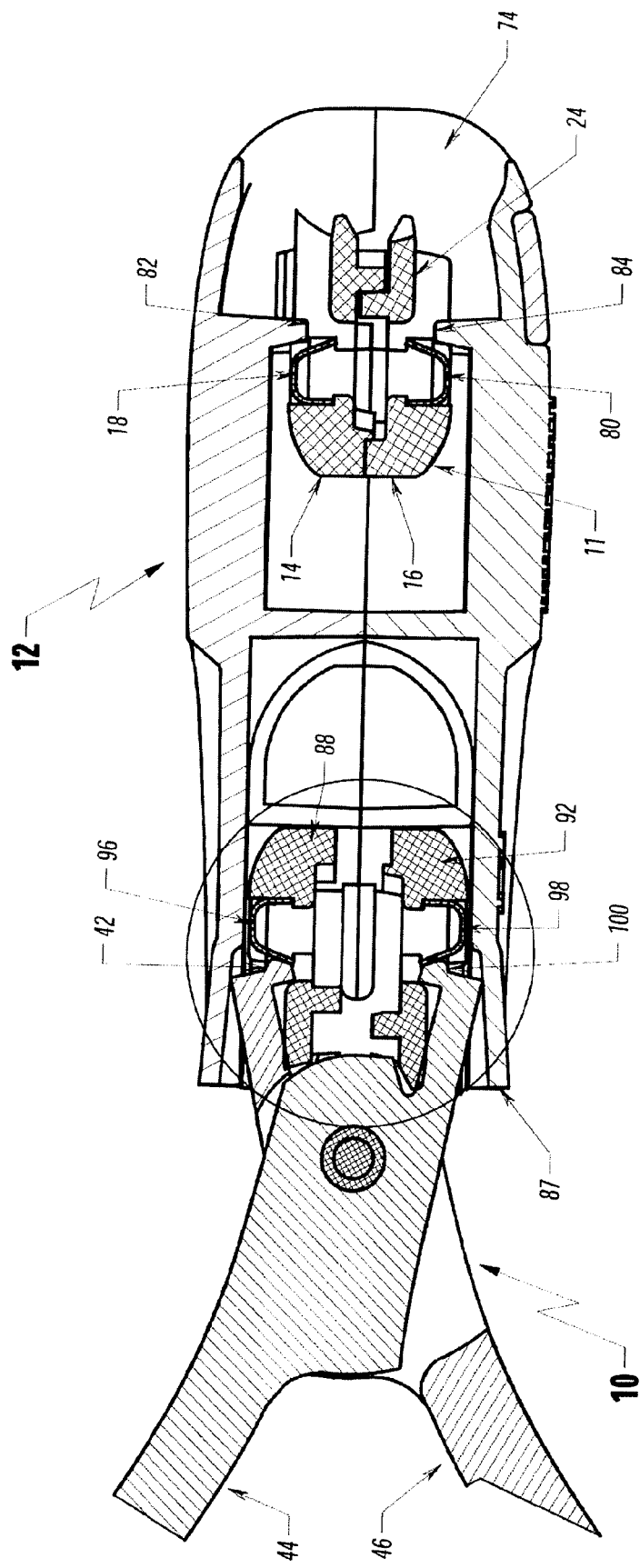
FIG. 26 is a cross-sectional view of FIG. 25.
Figure 27:
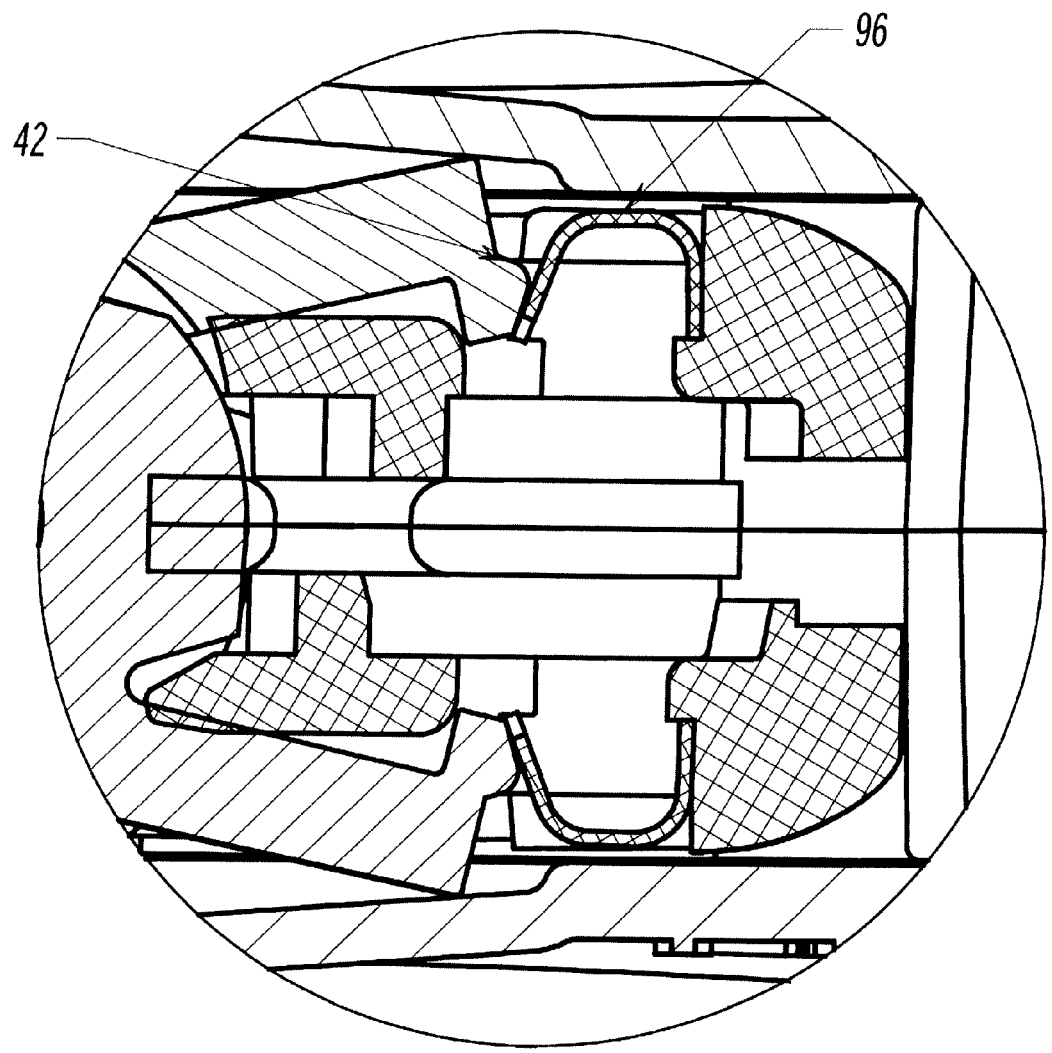
FIG. 27 is close up view of a section of FIG. 26.
Figure 28:
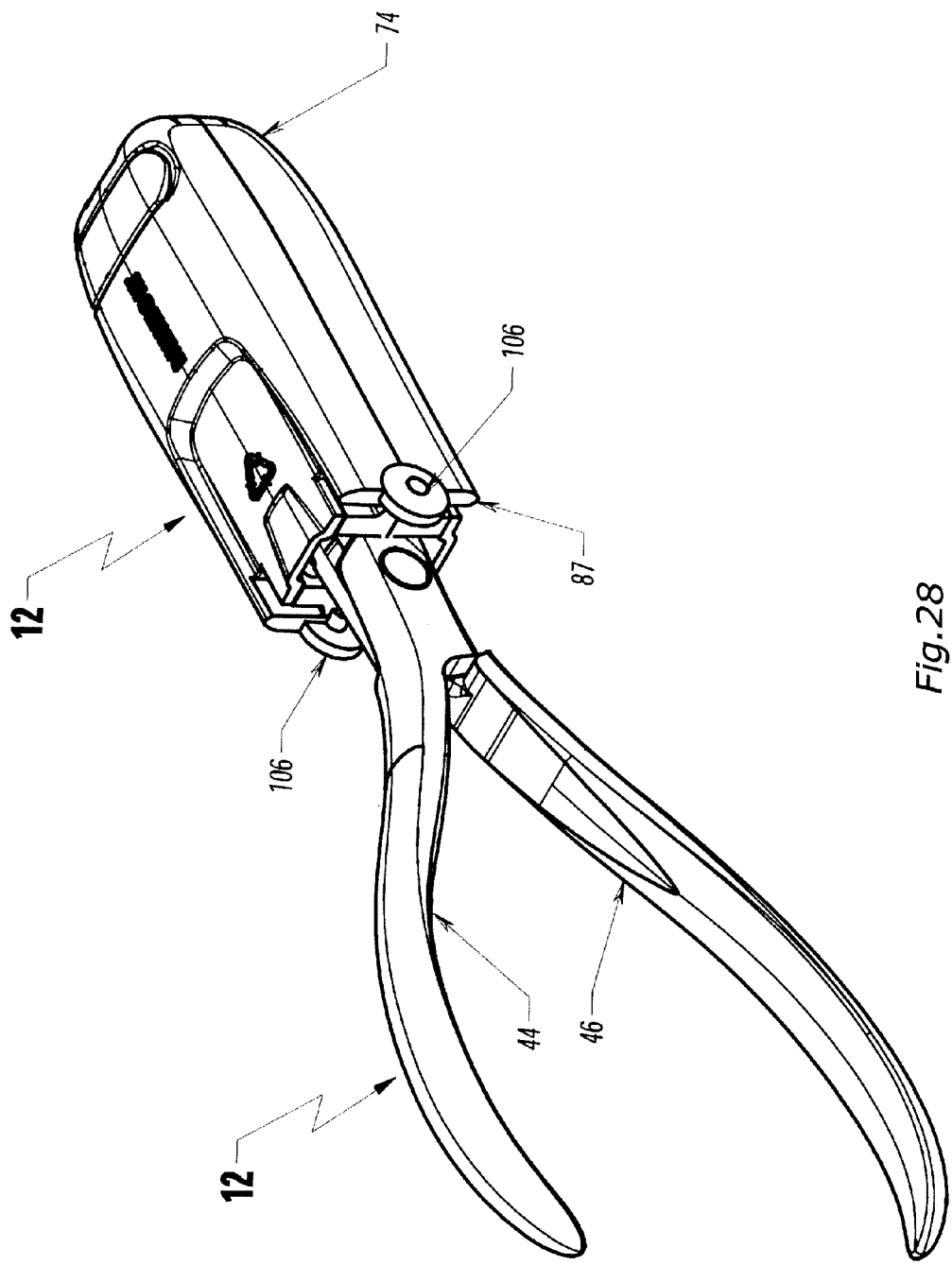
FIG. 28 is a perspective view of the hand tool and retooling device of FIG. 1, wherein the hand tool is being closed within the attachment side of the closed retooling device to attach the new head to the hand tool.
Figure 29:
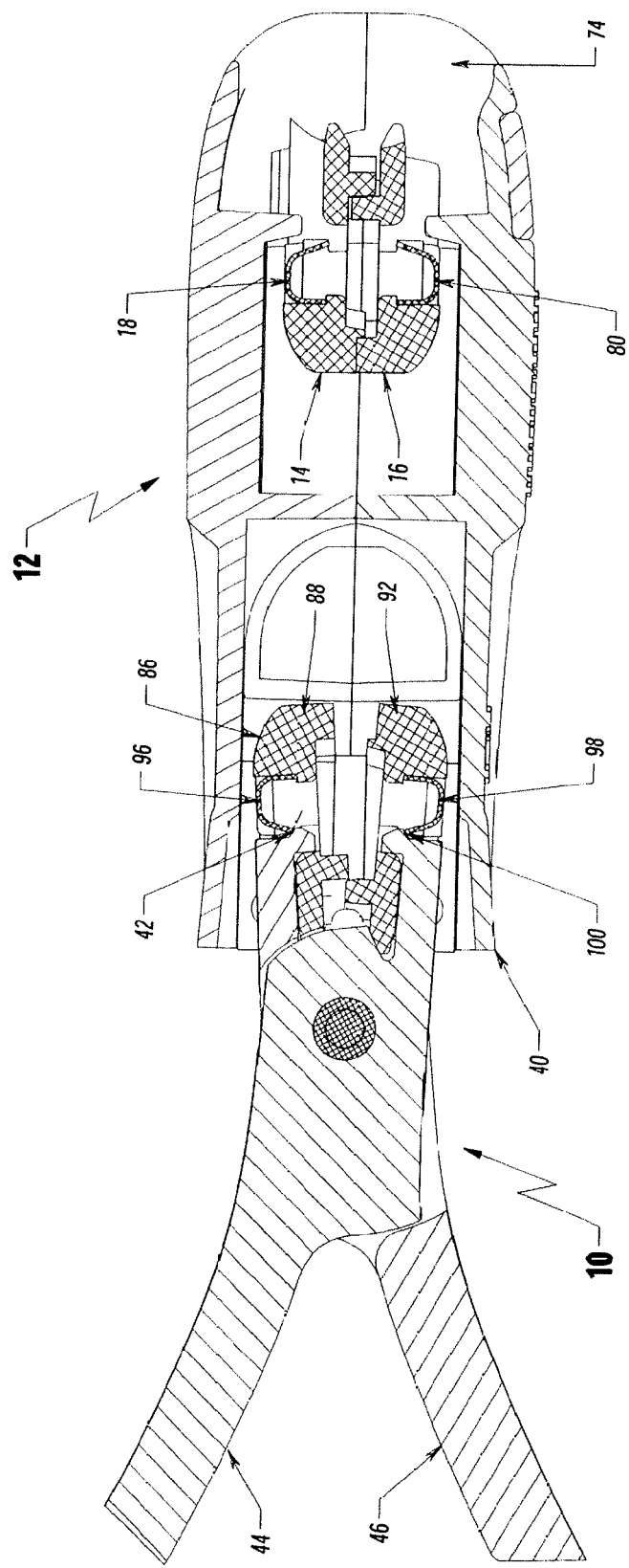
FIG. 29 is a cross-sectional view of FIG. 28.

As shown in FIGS. 25 and 26, to attach a new head to the hand tool 10, the user inserts the hand tool 10 into an attachment side 87. The new head comes pre-loaded in the retooling device 12 and is comprised of new upper jaw 88, new lower jaw 92 and associated springs 96 and 98. The new upper jaw 88 of the new head 86 is already located in an upper drawer 90 (see FIG. 1) and the new lower jaw 92 is already located into a lower drawer 94. The user (not shown) closes the handles 44 and 46, so that the spring connectors 96 and 98 abut against the ledges 42 and 100 (see FIG. 27).

Figure 30:
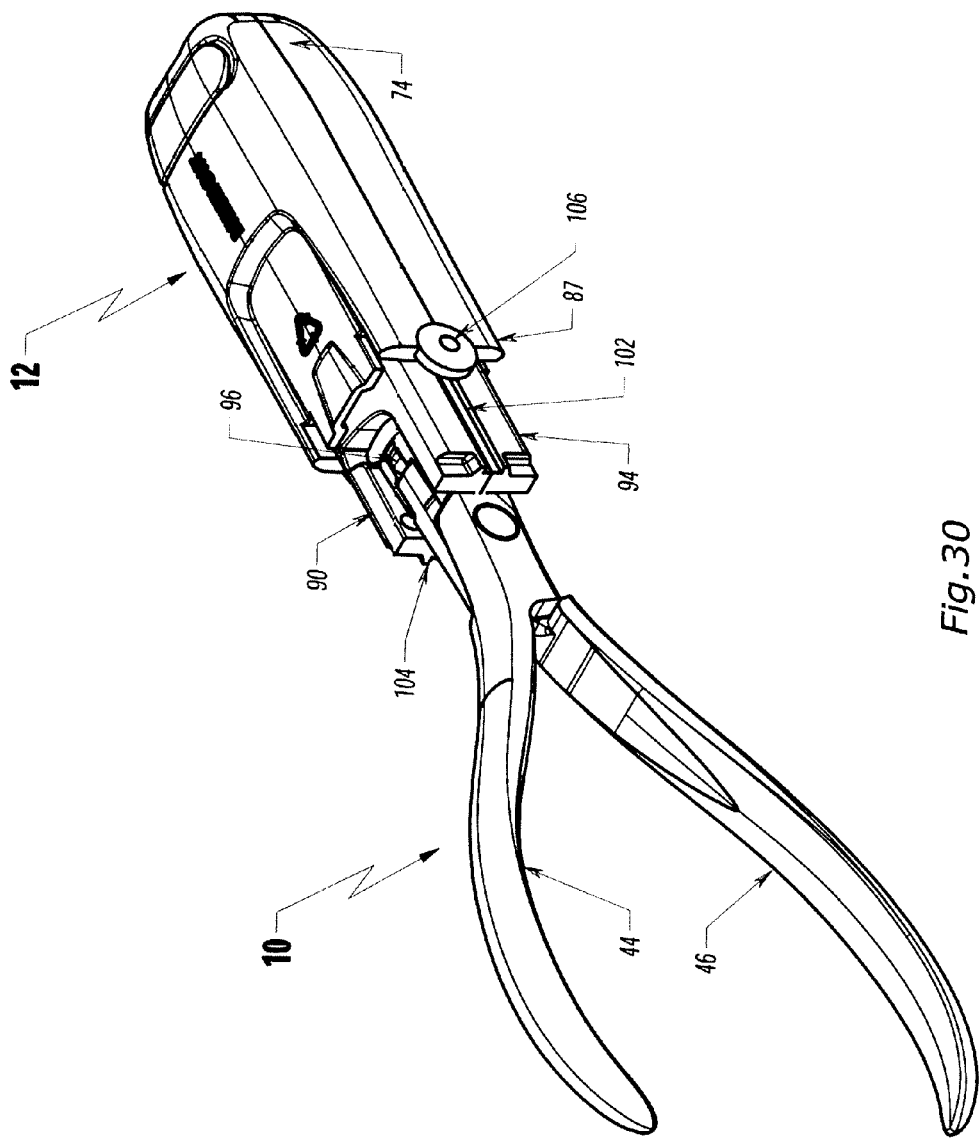
FIG. 30 is a perspective view of the hand tool and retooling device of FIG. 1, wherein the hand tool is in a closed position and being removed from the attachment side of the closed retooling device with the new head attached thereto.
Figure 31:
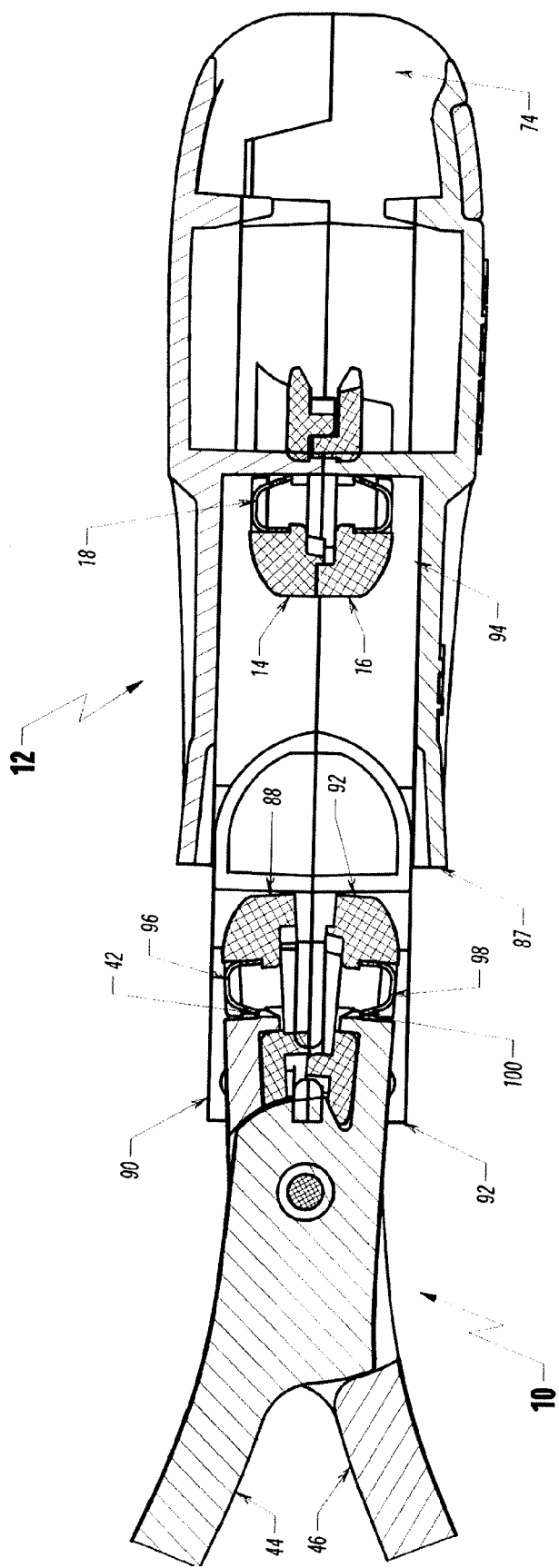
FIG. 31 is a cross-sectional view of FIG. 30.

Referring to FIGS. 30 and 31, to remove the new head of the hand tool 10 from the retooling device 12, the user withdraws the upper and lower drawers 90 and 94 from within the retooling device 12. The upper and lower drawers 90 and 92 have guides 102 and 104 with stops (not shown) which abut the hinge 106 to prevent the bottom and top drawers 90 and 92 from being completely withdrawn from the retooling device 12.

Figure 32:
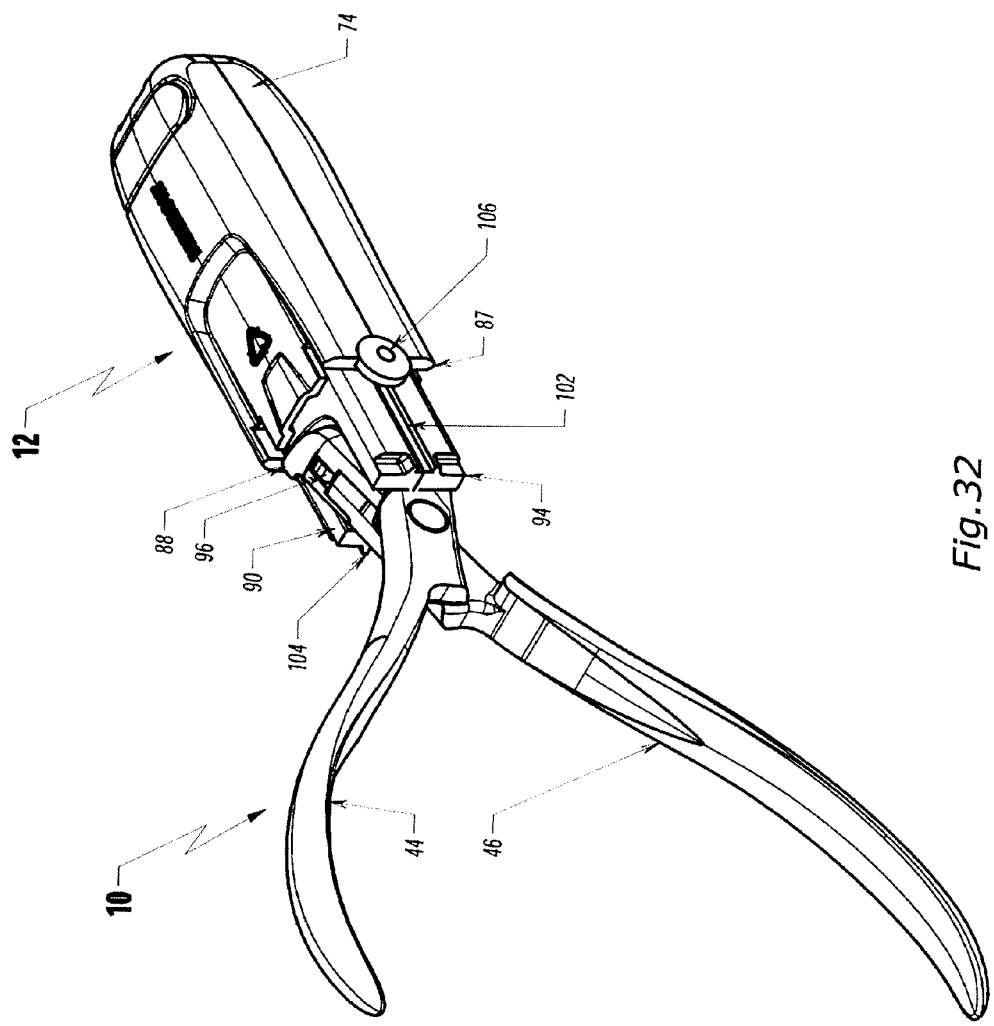
FIG. 32 is a perspective view of the hand tool and retooling device of FIG. 1, wherein the hand tool is in an open position and being removed from the attachment side of the closed retooling device with the new head attached thereto.
Figure 33:
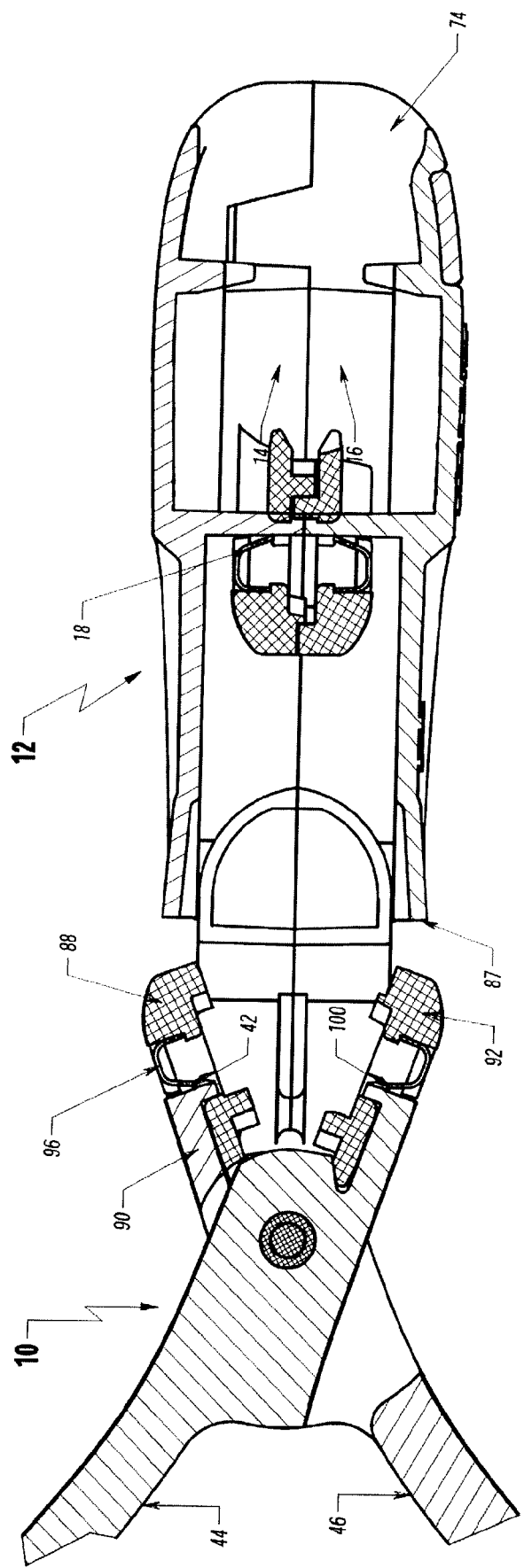
FIG. 33 is a cross-sectional view of FIG. 32.

The user is then able to open the handles 44 and 46 (see FIGS. 32 and 33), releasing the hand tool 10 from retooling device 12 with the new head attached thereto. The process of replacing the new head can be conducted in a sterile manner using the present invention as the user does not need to touch the head of the tool during the process of replacing the head of the tool.

Various modifications may be made in details of design and construction without departing from the scope and ambit of the invention.

INDUSTRIAL APPLICABILITY

The present invention has applications in the dental, surgical and medical industries. The present invention also applications for precision tools, mechanical and agricultural tools and even tools other than hand operated tools.

The invention claimed is:

1. A hand tool adapted to engage a retooling device for replacing at least one removeably attached part of the hand tool,
   wherein the at least one removeably attached part comprises a removeably attachable head which is attached to the hand tool via a connector that is actuated by an actuating member of the retooling device;
   wherein the connector is activated by the actuating member when force is applied to the hand tool which causes the connector to become biased against the actuating member;
   wherein the hand tool is adapted to engage the retooling device such that both removal and attachment of the removeably attachable head is effected using the one retooling device; and
   wherein the tool is a set of pliers and the at least one removably attached part comprises the head of the pliers.

2. A retooling device for removing and replacing at least one removeably attached part of a tool that is adapted to engage the retooling device, the retooling device comprising an actuating member for engaging a connector of the tool that when actuated detaches the at least one removeably attached part of the tool,
   wherein the retooling device comprises a body which is adapted to store at least one replacement part inside the retooling device;
   wherein the retooling device is adapted to apply a loaded at least one replacement part without a user touching the at least one replacement part; and
   wherein the retooling device is adapted to receive a tool with at least one removeably attached part for removal at a first end where the part is detached and stored in the body of the retooling device, and at a second end, receive a remaining portion of the tool and attach the replacement part.

3. The retooling device of claim 2 wherein the retooling device further comprises means to capture the at least one removeably attached part that is being replaced.

4. A retooling system comprising a retooling device and a tool adapted to engage the retooling device such that the tool can have at least one removeably attached part first detached then replaced with a replacement part by insertion into two ends of the retooling device.

5. The retooling system of claim 4 wherein the system provides the means for replacing the one replacement part without a user touching the replacement part.

6. A method of retooling a tool in need of a replacement part, the method comprising:
   inserting the tool into a first end of a retooling device and actuating the retooling device to detach the part to be replaced;
   removing the tool and inserting it into a second end of the retooling device and actuating the retooling device to attach the replacement part; and
   removing the tool from the retooling device with the replacement part attached.

7. The method of claim 6 wherein the tool comprises a set of pivoting handles and actuating the retooling device involves applying force to the handles such that one or more connectors of the tool become biased against one or more actuating members of the retooling device.

8. The method of claim 7 wherein the tool is a set of pliers.

* * * * *